(12) United States Patent
Kveen et al.

(10) Patent No.: US 8,050,774 B2
(45) Date of Patent: Nov. 1, 2011

(54) ELECTRODE APPARATUS, SYSTEMS AND METHODS

(75) Inventors: Graig L. Kveen, Maple Crove, MN (US); Roger N. Hastings, Maple Grove, MN (US); Anupama Sadasiva, Plymouth, MN (US); Vitaly N. Shapovalov, New Hope, MN (US); Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 266 days.

(21) Appl. No.: 11/316,120

(22) Filed: Dec. 22, 2005

(65) Prior Publication Data

US 2007/0150009 A1   Jun. 28, 2007

(51) Int. Cl.
A61N 1/05   (2006.01)
(52) U.S. Cl. .............. 607/122; 607/32; 607/33; 607/60; 607/61; 607/116; 600/381
(58) Field of Classification Search .................. 607/116, 607/122; 600/381
See application file for complete search history.

(56) References Cited

U.S. PATENT DOCUMENTS

| | | |
|---|---|---|
| 3,057,356 A | 10/1962 | Greatbatch |
| 3,357,434 A | 12/1967 | Abell |
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron et al. |
| 3,942,535 A | 3/1976 | Schulman |
| 3,943,936 A | 3/1976 | Rasor et al. |
| 4,157,720 A | 6/1979 | Greatbatch |
| 4,162,679 A | 7/1979 | Reenstierna |
| 4,198,991 A | 4/1980 | Harris |
| 4,256,115 A | 3/1981 | Bilitch |
| 4,441,210 A | 4/1984 | Hochmair et al. |
| 4,525,774 A | 6/1985 | Kino et al. |
| 4,641,664 A | 2/1987 | Botvidsson |
| 4,721,118 A | 1/1988 | Harris |

(Continued)

FOREIGN PATENT DOCUMENTS

EP   1166820 A2   1/2002

(Continued)

OTHER PUBLICATIONS

Busch, "On the Heating of Inductively Coupled Resonators (Stents) During MRI Examinations", Magnetic Resonance in Medicine, 2005, vol. 54, pp. 775-782.

(Continued)

*Primary Examiner* — Niketa Patel
*Assistant Examiner* — Joseph Stoklosa
(74) *Attorney, Agent, or Firm* — Schwegman, Lundberg & Woessner, P.A.

(57) ABSTRACT

Apparatus, system, and method that include a pacing apparatus having a stent electrode through which pulses of electrical current can be delivered. Stent electrodes receive energy for generating the electrical current from a variety of sources. Sources include from one or more induction coils that can form at least a portion of the stent. Sources can also include an implantable pulse generator coupled to a lead through which pulses of the electrical current are supplied to the stent electrodes.

14 Claims, 12 Drawing Sheets

U.S. PATENT DOCUMENTS

| | | | |
|---|---|---|---|
| 4,830,006 A | 5/1989 | Haluska et al. | |
| 4,953,564 A | 9/1990 | Berthelsen | |
| 4,987,897 A | 1/1991 | Funke | |
| 5,012,806 A | 5/1991 | De Bellis | |
| 5,078,736 A | 1/1992 | Behl | |
| 5,139,033 A | 8/1992 | Everett et al. | |
| 5,143,090 A | 9/1992 | Dutcher et al. | |
| 5,170,802 A | 12/1992 | Mehra | |
| 5,178,149 A | 1/1993 | Imburgia et al. | |
| 5,193,539 A | 3/1993 | Schulman et al. | |
| 5,193,540 A | 3/1993 | Schulman et al. | |
| 5,234,437 A | 8/1993 | Sepetka | |
| 5,250,071 A | 10/1993 | Palermo | |
| 5,255,693 A | 10/1993 | Dutcher et al. | |
| 5,261,916 A | 11/1993 | Engelson | |
| 5,300,107 A | 4/1994 | Stokes et al. | |
| 5,304,195 A | 4/1994 | Twyford, Jr. et al. | |
| 5,312,415 A | 5/1994 | Palermo | |
| 5,312,439 A | 5/1994 | Loeb | |
| 5,324,316 A | 6/1994 | Schulman et al. | |
| 5,324,325 A | 6/1994 | Moaddeb | |
| 5,336,252 A | 8/1994 | Cohen | |
| 5,342,408 A | 8/1994 | deCoriolis et al. | |
| 5,350,397 A | 9/1994 | Palermo et al. | |
| 5,383,915 A | 1/1995 | Adams | |
| 5,383,924 A | 1/1995 | Brehier | |
| 5,405,367 A | 4/1995 | Schulman et al. | |
| 5,411,535 A | 5/1995 | Fujii et al. | |
| 5,411,537 A | 5/1995 | Munshi et al. | |
| 5,447,533 A | 9/1995 | Vachon et al. | |
| 5,531,780 A | 7/1996 | Vachon | |
| 5,571,148 A | 11/1996 | Loeb et al. | |
| 5,622,168 A | 4/1997 | Keusch et al. | |
| 5,624,316 A | 4/1997 | Roskowski et al. | |
| 5,735,887 A | 4/1998 | Barreras, Sr. et al. | |
| 5,755,764 A | 5/1998 | Schroeppel | |
| 5,772,693 A | 6/1998 | Brownlee | |
| 5,775,331 A | 7/1998 | Raymond et al. | |
| 5,779,715 A | 7/1998 | Tu | |
| 5,800,535 A | 9/1998 | Howard, III | |
| 5,814,089 A | 9/1998 | Stokes et al. | |
| 5,833,715 A | 11/1998 | Vachon et al. | |
| 5,851,227 A | 12/1998 | Spehr | |
| 5,871,532 A | 2/1999 | Schroeppel | |
| 5,876,429 A | 3/1999 | Schroeppel | 607/115 |
| 6,035,239 A | 3/2000 | Patag et al. | |
| 6,053,873 A | 4/2000 | Govari et al. | |
| 6,115,636 A * | 9/2000 | Ryan | 607/60 |
| 6,123,724 A | 9/2000 | Denker | |
| 6,132,456 A | 10/2000 | Sommer et al. | |
| 6,141,588 A | 10/2000 | Cox et al. | |
| 6,141,591 A | 10/2000 | Lenarz et al. | |
| 6,161,029 A * | 12/2000 | Spreigl et al. | 600/381 |
| 6,164,284 A | 12/2000 | Schulman et al. | |
| 6,200,303 B1 | 3/2001 | Verrior et al. | |
| 6,208,894 B1 | 3/2001 | Schulman et al. | |
| 6,223,079 B1 | 4/2001 | Bakels et al. | |
| 6,240,316 B1 | 5/2001 | Richmond et al. | |
| 6,266,567 B1 | 7/2001 | Ishikawa et al. | |
| 6,315,721 B2 | 11/2001 | Schulman et al. | |
| 6,317,615 B1 * | 11/2001 | KenKnight et al. | 600/372 |
| 6,322,559 B1 * | 11/2001 | Daulton et al. | 606/41 |
| 6,336,937 B1 | 1/2002 | Vonesh et al. | |
| 6,345,202 B2 | 2/2002 | Richmond et al. | |
| 6,363,938 B2 | 4/2002 | Saadat et al. | |
| 6,370,434 B1 | 4/2002 | Zhang et al. | |
| 6,381,495 B1 | 4/2002 | Jenkins | |
| 6,385,472 B1 | 5/2002 | Hall et al. | |
| 6,409,674 B1 | 6/2002 | Brockway et al. | |
| 6,442,413 B1 | 8/2002 | Silver | |
| 6,445,953 B1 | 9/2002 | Bulkes et al. | |
| 6,456,256 B1 | 9/2002 | Amundson et al. | |
| 6,510,345 B1 | 1/2003 | Van | |
| 6,522,926 B1 | 2/2003 | Kieval et al. | 607/44 |
| 6,556,874 B2 | 4/2003 | Audoglio | |
| 6,564,807 B1 | 5/2003 | Schulman et al. | |
| 6,571,127 B1 | 5/2003 | Ben-Haim et al. | |
| 6,574,510 B2 | 6/2003 | Von Arx et al. | |
| 6,582,441 B1 | 6/2003 | He et al. | |
| 6,614,406 B2 | 9/2003 | Amundson et al. | |
| 6,647,291 B1 | 11/2003 | Bonner et al. | |
| 6,647,292 B1 | 11/2003 | Bardy et al. | |
| 6,765,144 B1 | 7/2004 | Wang et al. | 174/36 |
| 6,783,499 B2 | 8/2004 | Schwartz | |
| 6,895,265 B2 | 5/2005 | Silver | |
| 6,895,280 B2 | 5/2005 | Meadows et al. | |
| 6,901,294 B1 | 5/2005 | Whitehurst et al. | |
| 6,907,285 B2 | 6/2005 | Denker et al. | |
| 6,917,833 B2 * | 7/2005 | Denker et al. | 607/60 |
| 6,947,792 B2 | 9/2005 | Ben-Haim et al. | |
| 6,970,742 B2 | 11/2005 | Mann et al. | 607/23 |
| 6,971,391 B1 | 12/2005 | Wang et al. | 128/846 |
| 6,978,173 B2 | 12/2005 | Stoll et al. | |
| 7,003,350 B2 | 2/2006 | Denker et al. | |
| 7,076,305 B2 | 7/2006 | Imran et al. | |
| 7,209,783 B2 | 4/2007 | Fellows et al. | |
| 7,231,260 B2 | 6/2007 | Wallace et al. | |
| 7,532,932 B2 | 5/2009 | Denker et al. | |
| 7,532,933 B2 | 5/2009 | Hastings et al. | |
| 7,615,010 B1 | 11/2009 | Najafi et al. | |
| 7,647,109 B2 | 1/2010 | Hastings et al. | |
| 7,650,186 B2 | 1/2010 | Hastings et al. | |
| 2001/0018547 A1 | 8/2001 | Mechlenburg et al. | |
| 2002/0018379 A1 | 2/2002 | Hakuchoh et al. | |
| 2002/0026228 A1 * | 2/2002 | Schauerte | 607/122 |
| 2002/0065543 A1 | 5/2002 | Gomperz et al. | |
| 2002/0077685 A1 | 6/2002 | Sundquist et al. | |
| 2002/0123774 A1 | 9/2002 | Loeb et al. | |
| 2002/0123785 A1 | 9/2002 | Zhang et al. | |
| 2002/0128546 A1 | 9/2002 | Silver | |
| 2002/0138009 A1 | 9/2002 | Brockway et al. | |
| 2002/0138100 A1 | 9/2002 | Stoll et al. | |
| 2002/0183791 A1 * | 12/2002 | Denker et al. | 607/5 |
| 2002/0188323 A1 | 12/2002 | Penner et al. | 607/2 |
| 2002/0198604 A1 | 12/2002 | Schulman et al. | |
| 2003/0009093 A1 | 1/2003 | Silver | |
| 2003/0036773 A1 | 2/2003 | Whitehurst et al. | |
| 2003/0050681 A1 | 3/2003 | Pianca et al. | |
| 2003/0055465 A1 | 3/2003 | Ben-Haim et al. | |
| 2003/0055466 A1 | 3/2003 | Ben-Haim et al. | |
| 2003/0055467 A1 | 3/2003 | Ben-Haim et al. | |
| 2003/0088278 A1 | 5/2003 | Bardy et al. | |
| 2003/0109914 A1 | 6/2003 | Westlund et al. | |
| 2003/0114735 A1 | 6/2003 | Silver et al. | |
| 2003/0114742 A1 | 6/2003 | Lewkowicz et al. | |
| 2003/0158584 A1 * | 8/2003 | Cates et al. | 607/2 |
| 2003/0172388 A1 | 9/2003 | Fujise et al. | |
| 2003/0181958 A1 | 9/2003 | Dobak | |
| 2003/0181959 A1 | 9/2003 | Dobak | |
| 2003/0204206 A1 | 10/2003 | Padua et al. | 607/2 |
| 2003/0216729 A1 | 11/2003 | Marchitto et al. | |
| 2003/0236518 A1 | 12/2003 | Marchitto et al. | |
| 2004/0019364 A1 | 1/2004 | Kieval et al. | |
| 2004/0059280 A1 | 3/2004 | Makower et al. | |
| 2004/0059392 A1 | 3/2004 | Parramon et al. | |
| 2004/0073267 A1 | 4/2004 | Holzer | |
| 2004/0097805 A1 | 5/2004 | Verard et al. | 600/428 |
| 2004/0098068 A1 | 5/2004 | Carbunaru et al. | |
| 2004/0102830 A1 | 5/2004 | Williams | |
| 2004/0103906 A1 | 6/2004 | Schulman et al. | |
| 2004/0106954 A1 | 6/2004 | Whitehurst et al. | |
| 2004/0127895 A1 | 7/2004 | Flock et al. | |
| 2004/0147969 A1 | 7/2004 | Mann et al. | 607/17 |
| 2004/0147973 A1 | 7/2004 | Hauser | |
| 2004/0167580 A1 | 8/2004 | Mann et al. | 607/17 |
| 2004/0171355 A1 | 9/2004 | Yu et al. | |
| 2004/0172083 A1 | 9/2004 | Penner | |
| 2004/0176672 A1 | 9/2004 | Silver et al. | |
| 2004/0176822 A1 | 9/2004 | Thompson et al. | |
| 2004/0193092 A1 | 9/2004 | Deal | 604/8 |
| 2004/0193229 A1 | 9/2004 | Starkebaum et al. | |
| 2004/0210282 A1 | 10/2004 | Flock et al. | |
| 2004/0210289 A1 | 10/2004 | Wang et al. | |
| 2004/0215092 A1 | 10/2004 | Fischell et al. | |
| 2004/0230090 A1 | 11/2004 | Hegde et al. | |
| 2004/0230255 A1 | 11/2004 | Dobak, III | 607/58 |
| 2004/0230271 A1 | 11/2004 | Wang et al. | |

| | | |
|---|---|---|
| 2004/0249428 A1 | 12/2004 | Wang et al. |
| 2004/0254419 A1 | 12/2004 | Wang et al. |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0051243 A1 | 3/2005 | Forbes Jones et al. ........ 148/442 |
| 2005/0057905 A1 | 3/2005 | He et al. |
| 2005/0065575 A1 | 3/2005 | Dobak ........................ 607/45 |
| 2005/0079132 A1 | 4/2005 | Wang et al. |
| 2005/0080346 A1 | 4/2005 | Gianchandani et al. |
| 2005/0080459 A1 | 4/2005 | Jacobson et al. ................. 607/9 |
| 2005/0095197 A1 | 5/2005 | Tuszynski et al. ........... 424/1.11 |
| 2005/0096702 A1 | 5/2005 | Denker et al. |
| 2005/0107870 A1 | 5/2005 | Wang et al. |
| 2005/0131511 A1 | 6/2005 | Westlund |
| 2005/0136385 A1 | 6/2005 | Mann et al. .................... 434/320 |
| 2005/0149157 A1 | 7/2005 | Hunter et al. ................ 607/119 |
| 2005/0152946 A1 | 7/2005 | Hunter et al. ................ 424/423 |
| 2005/0154374 A1 | 7/2005 | Hunter et al. .............. 604/890.1 |
| 2005/0158356 A1 | 7/2005 | Hunter et al. ................ 424/423 |
| 2005/0165456 A1 | 7/2005 | Mann et al. ..................... 607/30 |
| 2005/0169960 A1 | 8/2005 | Hunter et al. ................ 424/423 |
| 2005/0169961 A1 | 8/2005 | Hunter et al. ................ 424/423 |
| 2005/0175664 A1 | 8/2005 | Hunter et al. ................ 424/423 |
| 2005/0175665 A1 | 8/2005 | Hunter et al. ................ 424/423 |
| 2005/0175703 A1 | 8/2005 | Hunter et al. ................ 424/486 |
| 2005/0178395 A1 | 8/2005 | Hunter et al. ................ 128/898 |
| 2005/0178396 A1 | 8/2005 | Hunter et al. ................ 128/898 |
| 2005/0181005 A1 | 8/2005 | Hunter et al. ................ 424/422 |
| 2005/0181009 A1 | 8/2005 | Hunter et al. ................ 424/423 |
| 2005/0181010 A1 | 8/2005 | Hunter et al. ................ 424/423 |
| 2005/0182450 A1 | 8/2005 | Hunter et al. ................. 607/36 |
| 2005/0182456 A1 | 8/2005 | Ziobro et al. |
| 2005/0182463 A1 | 8/2005 | Hunter et al. ................ 607/115 |
| 2005/0182465 A1 | 8/2005 | Ness |
| 2005/0182467 A1 | 8/2005 | Hunter et al. ................ 607/116 |
| 2005/0182468 A1 | 8/2005 | Hunter et al. ................ 607/116 |
| 2005/0182469 A1 | 8/2005 | Hunter et al. ................ 607/116 |
| 2005/0183731 A1 | 8/2005 | Hunter et al. ................ 128/898 |
| 2005/0186239 A1 | 8/2005 | Hunter et al. ................ 424/422 |
| 2005/0186244 A1 | 8/2005 | Hunter et al. ................ 424/423 |
| 2005/0186245 A1 | 8/2005 | Hunter et al. ................ 424/423 |
| 2005/0187140 A1 | 8/2005 | Hunter et al. ..................... 514/2 |
| 2005/0187600 A1 | 8/2005 | Hunter et al. ................ 607/115 |
| 2005/0192637 A1 | 9/2005 | Girouard et al. |
| 2005/0192647 A1 | 9/2005 | Hunter et al. ................. 607/57 |
| 2005/0196421 A1 | 9/2005 | Hunter et al. ................ 424/423 |
| 2005/0208095 A1 | 9/2005 | Hunter et al. ................ 424/423 |
| 2005/0209664 A1 | 9/2005 | Hunter et al. ................ 607/115 |
| 2005/0209665 A1 | 9/2005 | Hunter et al. ................ 607/115 |
| 2005/0209666 A1 | 9/2005 | Hunter et al. ................ 607/115 |
| 2005/0215764 A1 | 9/2005 | Tuszynski et al. ............. 530/358 |
| 2005/0245846 A1 | 11/2005 | Casey ........................ 600/585 |
| 2005/0249667 A1 | 11/2005 | Tuszynski et al. |
| 2005/0251238 A1 | 11/2005 | Wallace et al. |
| 2005/0251240 A1 | 11/2005 | Doan |
| 2005/0256549 A1 | 11/2005 | Holzer |
| 2005/0260331 A1 | 11/2005 | Wang et al. ..................... 427/2.1 |
| 2005/0261741 A1 | 11/2005 | Libbus et al. |
| 2005/0273014 A1 | 12/2005 | Gianchandani et al. |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Soykan et al. |
| 2006/0136001 A1 | 6/2006 | Ortega et al. |
| 2006/0136004 A1 | 6/2006 | Cowan et al. |
| 2006/0206170 A1* | 9/2006 | Denker et al. ................. 607/60 |
| 2007/0075905 A1 | 4/2007 | Denker et al. |
| 2007/0106357 A1* | 5/2007 | Denker et al. ................ 607/116 |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2008/0021505 A1 | 1/2008 | Hastings et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1* | 5/2008 | Rosero ........................ 607/62 |
| 2009/0204170 A1 | 8/2009 | Hastings et al. |
| 2009/0234407 A1 | 9/2009 | Hastings et al. |

FOREIGN PATENT DOCUMENTS

| | | |
|---|---|---|
| EP | 1166832 A1 | 1/2002 |
| EP | 0 904 009 | 9/2003 |
| EP | 1 264 572 | 8/2005 |
| EP | 1809372 A1 | 7/2007 |
| EP | 1812104 A1 | 8/2007 |
| EP | 1835962 A1 | 9/2007 |
| FR | 2559391 | 8/1985 |
| JP | 05076501 A2 | 3/1993 |
| NZ | 526115 | 10/2006 |
| NZ | 539770 | 10/2007 |
| NZ | 539771 | 10/2007 |
| WO | WO 91/16864 | 11/1991 |
| WO | WO 96/39932 | 12/1996 |
| WO | WO 97/45157 | 12/1997 |
| WO | WO-9826840 A1 | 6/1998 |
| WO | WO 98/29030 | 7/1998 |
| WO | WO 98/57592 | 12/1998 |
| WO | WO 99/03533 | 1/1999 |
| WO | WO-9906102 A1 | 2/1999 |
| WO | WO-9964104 A1 | 12/1999 |
| WO | WO 00/30534 | 6/2000 |
| WO | WO-0100114 A1 | 1/2001 |
| WO | WO 01/87137 | 11/2001 |
| WO | WO-03041793 A2 | 5/2003 |
| WO | WO-03053491 A2 | 7/2003 |
| WO | WO-03076010 A1 | 9/2003 |
| WO | WO 03/082403 | 10/2003 |
| WO | WO 03/096918 | 11/2003 |
| WO | WO 03/099102 | 12/2003 |
| WO | WO-2004002572 A1 | 1/2004 |
| WO | WO 2004/032788 | 4/2004 |
| WO | WO 2004/078025 | 9/2004 |
| WO | WO 2005/058143 | 6/2005 |
| WO | WO 2005/096954 | 10/2005 |
| WO | WO-2005101660 A1 | 10/2005 |
| WO | WO 2005/107852 | 11/2005 |
| WO | WO 2005/107863 | 11/2005 |
| WO | WO 2005/117737 | 12/2005 |
| WO | WO-2006045073 A1 | 4/2006 |
| WO | WO-2006045074 A2 | 4/2006 |
| WO | WO-2006045075 A1 | 4/2006 |
| WO | WO 2006/096685 | 9/2006 |
| WO | WO-2007067231 A1 | 6/2007 |
| WO | WO-2007067253 A1 | 6/2007 |
| WO | WO-2007078770 A2 | 7/2007 |
| WO | WO-2007115044 A2 | 10/2007 |
| WO | WO-2007115044 A3 | 10/2007 |
| WO | WO-2008011626 A1 | 1/2008 |
| WO | WO-2008034005 A2 | 3/2008 |
| WO | WO-2008034005 A3 | 3/2008 |
| WO | WO-2008111998 A1 | 9/2008 |
| WO | WO-2009099597 A1 | 8/2009 |

OTHER PUBLICATIONS

Busch, Martin, et al. "On the Heating of Inductively Coupled Resonators (Stents) During MRI Examinations". Magnetic Resonance in Medicine, 54 (2005), 775-782.

"U.S. Appl. No. 11/490,916 Restriction Requirement mailed Dec. 11, 2008", 8 pgs.

"Telemetry Research Transcutaneous Energy Transfer (TET) Technology Summary", *Telemetry Research Ltd.*, www.telemetryresearch.com, (No date listed), 1 pg.

Manoharan, G., et al., "Novel passive implantable atrial defibrillator using transcutaneous radiofrequency energy transmission successfully cardioverts atrial fibrillation.", *Circulation*, 108(11), (Sep. 16, 2003), 1382-8.

Piella, J. P., "Energy management, wireless and system solutions for highly integrated implantable devices", *Doctoral Thesis, Universitat Autonoma de Barcelona*, (Dec. 2001), 62 pgs.

Si, Ping, et al., "A Frequency Control Method for Regulating Wireless Power to Implantable Devices", *IEEE Transactions on Biomedical Circuits and Systems*, 2(1), (Mar. 2008), 22-29.

Swain, E., "Breakthrough Products Could Put Lesser-Known Firms on the Map", (c) *2004 Medical Device & Diagnostic Industry*, [online]. Retrieved from the Internet: <URL:http://www.devicelink.com/mddi/archive/04/04/006.html>, (Apr. 2004), 6 pgs.

Wagner, "Electrodes, Leads, and Biocompatibility", *Design of Cardiac Pacemakers*, chapter 6 and TOC, (1993), 133-160.

06847612.6, "European Application Serial No. 06847612.6Office Action mailed on May 26, 2009", 3 pgs.

"U.S. Appl. No. 10/971,550, Amendment Under 37 C.F.R. Sec. 1.312 filed Mar. 20, 2009", 6 pgs.

"U.S. Appl. No. 11/075,375, Response filed Jul. 16, 2009 to Final Office Action mailed Apr. 16, 2009", 13 pgs.

"U.S. Appl. No. 11/075,376, Notice of Allowance mailed Aug. 24, 2009", 6 pgs.

"U.S. Appl. No. 11/394,601, Final Office Action mailed Mar. 22, 2010", 7 pgs.

"U.S. Appl. No. 11/394,601, Non-Final Office Action mailed Sep. 2, 2009", 6 pgs.

"U.S. Appl. No. 11/394,601, Response filed Dec. 2, 2009 to Non Final Office Action mailed Sep. 2, 2009", 11 pgs.

"U.S. Appl. No. 11/490,576, Non-Final Office Action mailed Oct. 5, 2009", 8 pgs.

"U.S. Appl. No. 11/490,576, Response filed Mar. 5, 2010 to Non Final Office Action mailed Oct. 5, 2009", 13 pgs.

"U.S. Appl. No. 11/490,916, Final Office Action mailed Dec. 17, 2009", 11 pgs.

"U.S. Appl. No. 11/490,916, Response filed Sep. 3, 2009 to Non Final Office Action mailed May 5, 2009", 13 pgs.

"U.S. Appl. No. 11/511,152, Final Office Action mailed Aug. 10, 2009", 13 pgs.

"U.S. Appl. No. 11/511,152, Non-Final Office Action mailed Dec. 30, 2009", 13 pgs.

"U.S. Appl. No. 11/511,152, Response filed Nov. 12, 2009 to Final Office Action mailed Aug. 10, 2009", 13 pgs.

"U.S. Appl. No. 11/549,352, Appeal Brief filed Sep. 9, 2009", 36 pgs.

"U.S. Appl. No. 11/683,577, Final Office Action mailed Nov. 9, 2009", 14 pgs.

"U.S. Appl. No. 11/683,577, Response filed Aug. 5, 2009 to Non Final Office Action mailed Mar. 5, 2009", 10 pgs.

"U.S. Appl. No. 11/683,584, Final Office Action mailed Jan. 29, 2010", 9 pgs.

"U.S. Appl. No. 11/745,070, Final Office Action mailed Dec. 11, 2009", 18 pgs.

"U.S. Appl. No. 11/745,070, Response filed Jul. 27, 2009 to Non Final Office Action mailed Apr. 27, 2009", 11 pgs.

"U.S. Appl. No. 11/745,105, Final Office Action mailed Mar. 30, 2010", 9 pgs.

"U.S. Appl. No. 11/745,105, Non-Final Office Action mailed Sep. 18, 2009", 9 pgs.

"U.S. Appl. No. 11/745,105, Response filed Jan. 19, 10 to Non Final Office Action mailed Sep. 18, 2009", 12 pgs.

"U.S. Appl. No. 11/745,105, Response filed Jun. 22, 2009 to Restriction Requirement mailed May 21, 2009", 6 pgs.

"U.S. Appl. No. 11/745,105, Restriction Requirement mailed May 21, 2009", 6 pgs.

"U.S. Appl. No. 10/971,550, Examiner Interview Summary mailed Jan. 22, 2008", 4 pgs.

"U.S. Appl. No. 11/075,375, Examiner Interview Summary mailed Jan. 12, 2009", 4 pgs.

"U.S. Appl. No. 11/075,375, Examiner Interview Summary mailed May 1, 2008", 4 pgs.

"U.S. Appl. No. 11/075,375, Notice of Allowance mailed Sep. 4, 2009", 6 pgs.

"U.S. Appl. No. 11/075,376, Examiner Interview Summary mailed Jan. 12, 2009", 4 pgs.

"U.S. Appl. No. 11/075,376, Examiner Interview Summary mailed Apr. 2, 2008", 4 pgs.

"U.S. Appl. No. 11/394,601, Pre-Appeal Brief Request filed Jul. 21, 2010", 5 pgs.

"U.S. Appl. No. 11/490,576, Non-Final Office Action mailed Jul. 12, 2010", 9 pgs.

"U.S. Appl. No. 11/490,916, Examiner Interview Summary mailed Apr. 12, 2010", 3 pgs.

"U.S. Appl. No. 11/490,916, Examiner Interview Summary mailed Aug. 19, 2009", 2 pgs.

"U.S. Appl. No. 11/490,916, Notice of Allowance mailed Jul. 9, 2010", 4 pgs.

"U.S. Appl. No. 11/490,916, Response filed Jan. 12, 2009 to Restriction Requirement Jan. 12, 2009", 7 pgs.

"U.S. Appl. No. 11/490,916, Response filed Apr. 15, 2010 to Final Office Action mailed Dec. 17, 2009", 12 pgs.

"U.S. Appl. No. 11/511,152, Notice of Allowance mailed Jul. 28, 2010", 6 pgs.

"U.S. Appl. No. 11/511,152, Preliminary Amendment filed Oct. 17, 2006", 3 pgs.

"U.S. Appl. No. 11/511,152, Response filed Jun. 30, 2010 to Non-Final Office Action mailed Dec. 30, 2009", 12 pgs.

"U.S. Appl. No. 11/549,352, Examiner Interview Summary mailed Jun. 25, 2008", 2 pgs.

"U.S. Appl. No. 11/549,352, Examiner's Answer mailed Nov. 27, 2009 to Appeal Brief filed Sep. 9, 2009", 12 pgs.

"U.S. Appl. No. 11/549,352, Reply Brief filed Jan. 27, 2010", 8 pgs.

"U.S. Appl. No. 11/683,577, Examiner Interview Summary mailed Jul. 7, 2009", 4 pgs.

"U.S. Appl. No. 11/683,577, Response filed May 7, 2010 to Final Office Action mailed Nov. 9, 2009", 14 pgs.

"U.S. Appl. No. 11/683,584, Examiner Interview Summary mailed Jul. 7, 2009", 4 pgs.

"U.S. Appl. No. 11/683,584, Preliminary Amendment filed Mar. 8, 2007", 1 pg.

"U.S. Appl. No. 11/683,584, Response filed Jul. 21, 2010 to Final Office Action mailed Jan. 29, 2010", 12 pgs.

"U.S. Appl. No. 11/745,105, Response filed Jul. 29, 2010 to Final Office Action mailed Mar. 30, 2010", 12 pgs.

* cited by examiner

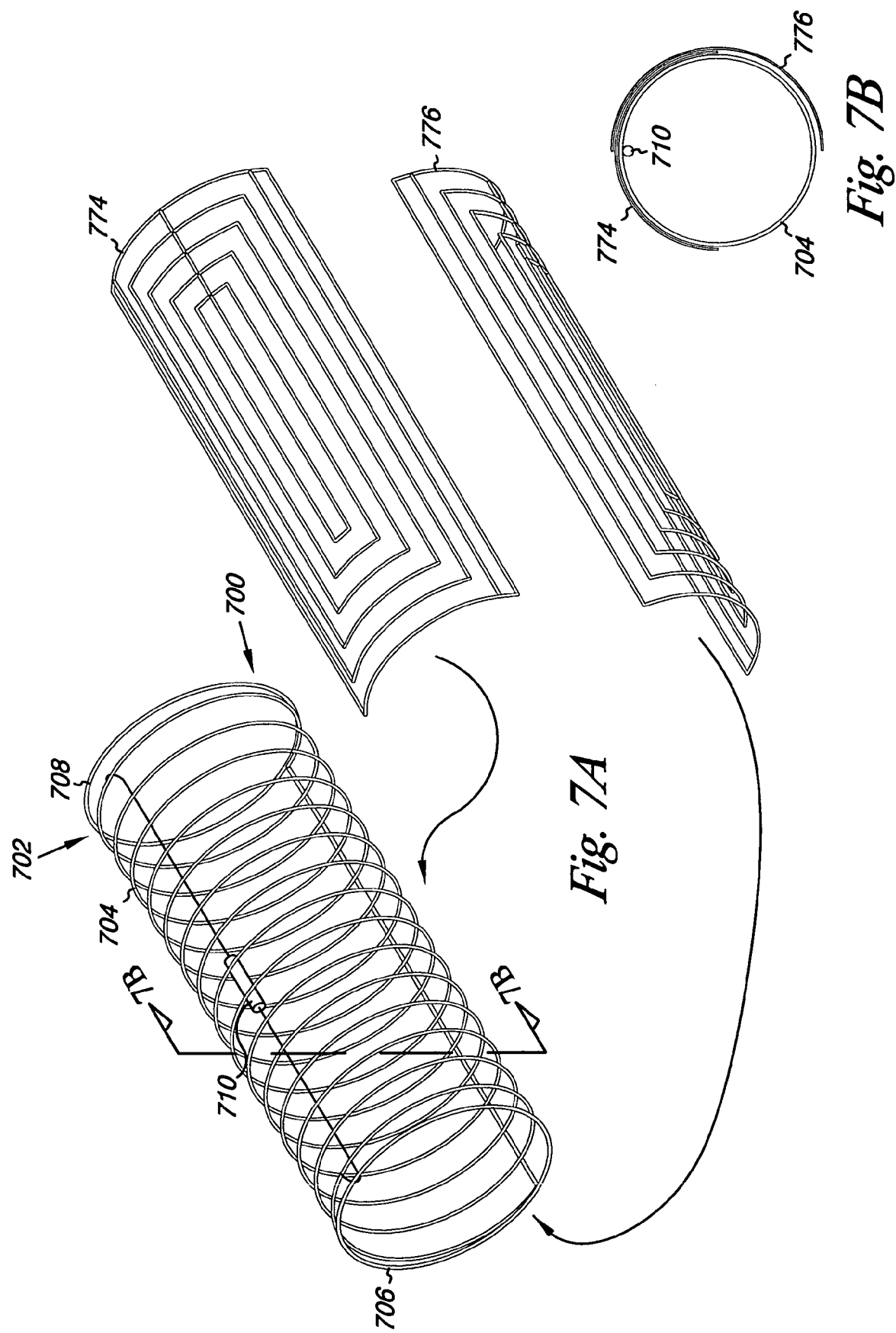

ELECTRODE APPARATUS, SYSTEMS AND METHODS

FIELD OF THE DISCLOSURE

The present disclosure relates generally to medical apparatus, systems, and methods for use with a mammalian heart; and more particularly to apparatus, systems, and methods for providing pulses of coordinated electrical current to the chambers of the mammalian heart.

BACKGROUND OF THE DISCLOSURE

In heart failure, the heart does not pump blood as well as it should and fluid builds up in the lungs. The symptoms of heart failure include difficulty breathing, decreased ability to exercise, and leg swelling. Although many drugs help patients with heart failure, there is no cure. The condition is disabling and even fatal for many patients.

In patients with heart failure, conduction of electrical impulses through the heart is often abnormal. This abnormal conduction, in turn, can lead to uncoordinated contraction of the ventricles, the large pumping chambers of the heart. Cardiac resynchronization, or atrial-synchronized biventricular pacing, has been shown to be an effective treatment for patients with moderate-to-severe heart failure.

Cardiac resynchronization is a heart failure treatment that uses a special type of pacemaker to synchronize the contraction of the ventricles. Results from resynchronization therapy studies on patients with New York Heart Association (NYHA) class III and IV heart failure have demonstrated significant improvement in the quality of life, functional status, and exercise capacity. In these patients, cardiac resynchronization has also been shown to improve cardiac structure and function while significantly reducing the risk of worsening heart failure.

Another serious cardiac condition is atrial fibrillation (AFIB). AFIB is a debilitating rapid and uncoordinated or chaotic depolarization of the atria, resulting in irregular contraction of the ventricles. In this condition, the atria are not capable of efficient ejection of blood into the ventricles during atrial systole, and blood tends to collect and stagnate in the atria. Patients with chronic AFIB are generally placed on life long systemic anticoagulation medication to prevent the formation of blood clots in the non-functional atria. AFIB is a common ailment among the aging population.

An even more serious cardiac condition is ventricular fibrillation (VFIB). VFIB is a rapid and uncoordinated or chaotic depolarization of the ventricles. In this condition, the ventricles are not capable of efficient ejection of blood, often resulting in sudden death of the subject. Patients at risk for VFIB often receive an implanted cardiac defibrillator.

Both AFIB and VFIB can be caused by an ectopic focal stimulation source arising from aberrant cells in the myocardium. For example, in the majority of AFIB, the abnormal cells giving rise to the condition are located in or around the openings of the pulmonary veins. Both AFIB and VFIB can manifest as racetrack patterns of depolarization in which depolarization traverses an irregular path through the tissues. In both conditions, depolarization is no longer controlled by the sinus node.

BRIEF DESCRIPTION OF THE DRAWINGS

FIGS. 7A-7C provide illustrations of additional embodiments of the pacing apparatus according to the present disclosure, where FIG. 7A is shown in an exploded view and FIG. 7B is an end view of the pacing apparatus illustrated in FIG. 7A.

DETAILED DESCRIPTION

Figure 1:
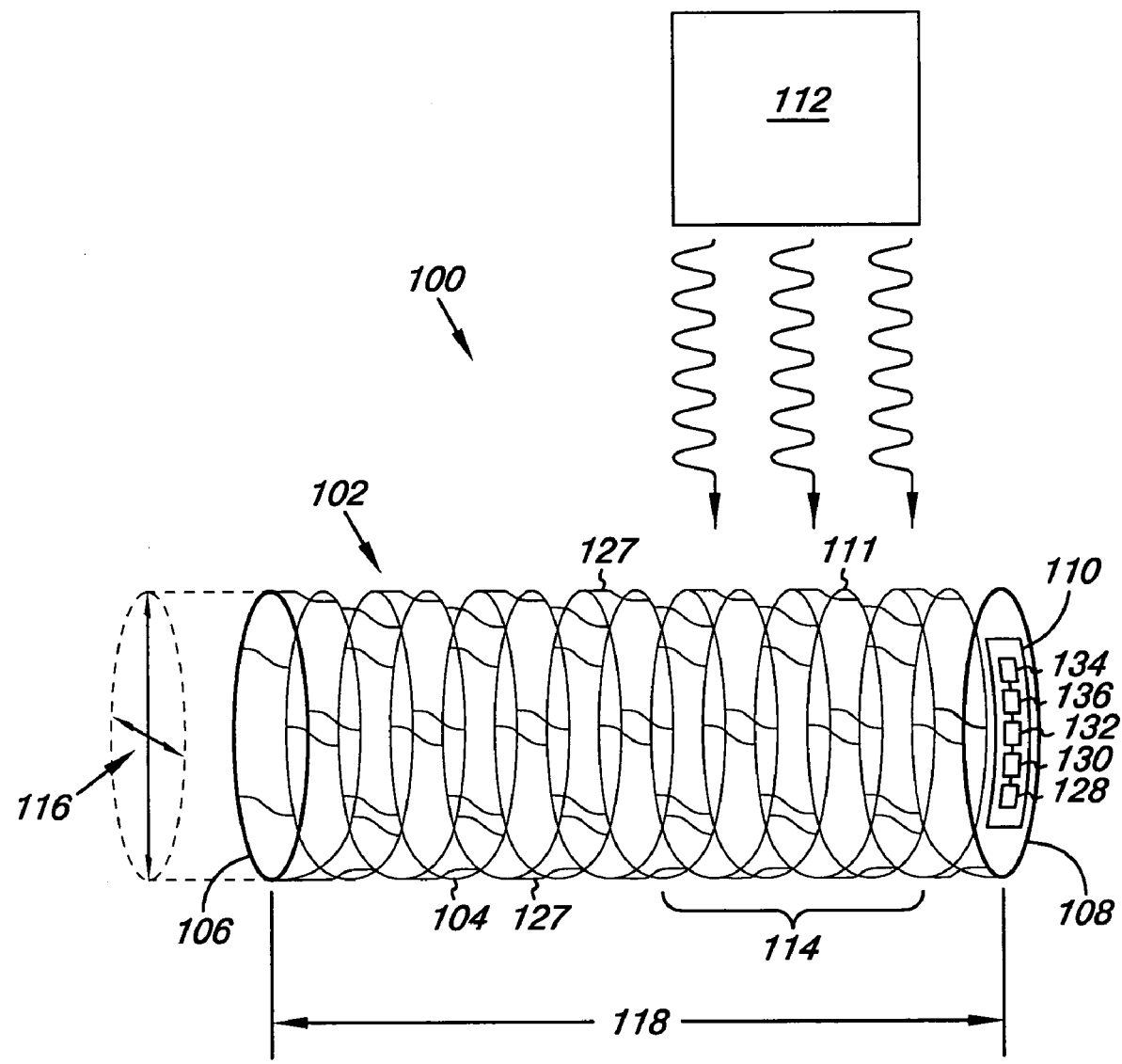
FIG. 1 provides an illustration of one embodiment of a pacing apparatus according to the present disclosure.

There are several heart conditions that may benefit from pacing at multiple sites of heart tissue. Such conditions include atrial fibrillation, ventricular fibrillation, and congestive heart failure (CHF). For example, it has been found that CHF patients have benefited from bi-ventricular pacing, that is, pacing of both the left ventricle and the right ventricle in a timed relationship. Such therapy has been referred to as "cardiac resynchronization therapy" or "CRT." CRT has been accomplished by placing conventional pacing leads in the right atrium and right ventricle, and placing a third lead over the left ventricle within a coronary vein. The venous lead extends from the CRT pacemaker, through the superior vena cava, and into the ostium of the coronary sinus, projecting through the coronary sinus to the left side of the heart, and into a lateral descending branch of the coronary venous system. The distal vein is generally occluded at the site of pacing. The venous pacing site on the left ventricle is used because pacing leads within the left ventricle are contraindicated. This is because of the high risk of thromboemboli forming on left ventricular leads that may result in a stroke.

It is believed that patients could benefit if multiple sites in the left and right ventricles could be synchronously paced in a programmed or timed relationship to one another. In addition, pacing at multiple sites may be beneficial where heart tissue through which electrical energy must propagate is scarred or dysfunctional, which condition halts or alters the propagation of an electrical signal through that heart tissue. In these cases multiple-site pacing may be useful to restart the propagation of the electrical signal immediately downstream of the dead or sick tissue area.

Synchronized pacing at multiple sites on the heart may inhibit the onset of fibrillation resulting from slow or aberrant conduction, thus reducing the need for implanted or external cardiac defibrillators. Arrhythmias may result from slow conduction or enlargement of the heart chamber. In these diseases, a depolarization wave that has taken a long and/or slow path around a heart chamber may return to its starting point after that tissue has had time to re-polarize. In this way, a never ending "race-track" or "circus" wave may exist in one or more chambers that is not synchronized with normal sinus rhythm. Atrial fibrillation, a common condition, may often be associated with such conduction abnormalities. Pacing at a sufficient number of sites in one or more heart chambers, for example in the atria, may force all tissue to depolarize in a synchronous manner to prevent the race-track and circus rhythms that lead to fibrillation.

Extending pacing leads to multiple sites over the left side of the heart would require multiple leads to be placed in the coronary venous system. Multiple leads in the coronary sinus may occlude too large of an area of that vessel. Even the presence of more than three leads extending through the superior vena cava could seriously obstruct that vessel.

Embodiments of the present disclosure are directed to an apparatus, system, and method for treating heart conditions such as congestive heart failure and atrial fibrillation. In addition, the embodiments of the present disclosure can be used in treating patients who have had an acute myocardial infarction, in addition to other causes of left ventricular failure from other diseases such as idiopathic dilated cardiomyopathy, restrictive cardiomyopathy, hypertrophic cardiomyopathy, and viral cardiomyopathy.

The present disclosure provides multiple electrodes to sites in the coronary venous and/or arterial system. In one embodiment, the electrodes are wireless, receiving stimulation energy from a source of radio frequency energy that is located outside the heart. In some cases the wireless electrodes are mounted on stents, thereby providing an open lumen through the stent for blood flow. For example, wireless stent electrodes may be placed in one or more of the pulmonary veins, the source of a majority of AFIB, to re-synchronize the beating of the left atrium.

More specifically, embodiments of the present disclosure include stent electrodes implanted within the coronary vasculature to provide pulses of coordinated electrical current (e.g., a pacing pulse) to the chambers of the heart. As discussed herein, embodiments of the stent electrodes receive energy for generating the electrical current from a variety of sources. For example, in one embodiment the stent electrodes generate the electrical current through the use of one or more induction coils that form at least a portion of the stent. In an additional embodiment, the one or more induction coils for generating the electrical current can be positioned at least partially on the stent. In an alternative embodiment, the stent electrode is coupled to a lead through which the electrical current is supplied.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of value. In addition, discussion of features and/or attributes for an element with respect to one FIG. can also apply to the element shown in one or more additional FIGS.

FIG. 1 provides an illustration of one embodiment of a pacing apparatus 100 according to the present disclosure. As illustrated, the pacing apparatus 100 includes a stent 102 having an induction coil structure 104. The pacing apparatus 100 further includes first and second electrodes 106 and 108 associated with the stent 102. As will be discussed herein, the electrodes 106 and 108 can be used to discharge an electrical current generated with the induction coil structure 104 of the stent 102 through the use of a control circuit 110.

As illustrated, the induction coil structure 104 extends circumferentially along a longitudinal axis of the stent 102. In other words, the induction coil structure 104 has a helical configuration. As will be appreciated, other configurations are possible, as will be illustrated herein. For example, the induction coil structure 104 of FIG. 1 could form at least a portion of the structural members of the stent 102, or alternatively, the coil 104 could lie on and be attached to a stent 102 having structural members that are separate from the coil structure 104.

The embodiment of FIG. 1 also illustrates the electrodes 106 and 108 positioned on an exterior surface 111 of the stent 102 so as to face radially away from the lumen of the stent 102. In one embodiment, the electrodes 106 and 108 are positioned in this fashion so as to minimize the exposure of the electrodes 106 and 108 to blood that will be flowing through the lumen of the stent 102 and to maximize the exposure of the adjacent myocardial tissue to the electrodes 106 and 108 once positioned within the coronary vasculature of the heart.

In addition, the electrodes 106 and 108 are illustrated as having a ring structure. As will be appreciated, the electrodes 106 and 108 can have one or more different structures such as partial ring, spherical, or partial spherical coupled in common.

The control circuit 110 can also be positioned at a number of different locations relative the stent 102. For example, as illustrated the control circuit 110 can be located between adjacent members of the induction coil structure 104. Alternatively, the control circuit 110 can be located at an end of the stent 102. In additional embodiments, the control circuit 110 could be suspended within the lumen of the stent 102. Alternatively, control circuit 110 could be incorporated within the material of stent structure 102. In an additional embodiment, the control circuit can be located away from the stent 102 and/or the induction coil structure 104. For example, the control circuit could be located in a magnetic field source 112, as will be discussed herein. Elements of the control circuit 110 (e.g., 134, 136, 132, 130, and 128) will be also be discussed more fully herein (e.g. with respect to FIG. 4).

In one embodiment, the induction coil structure 104 can be inductively coupled to a magnetic field source 112 generating a time-varying current at the location of induction coil structure 104. As will be discussed herein, a variety of devices for generating the current from the magnetic field source 112 are possible. As will be appreciated, a magnetic field generated by a pulsed alternating current (AC) or a pulsed direct current (DC) may be used in providing the magnetic field source 112. The resulting current induced through the induction coil structure 104 would likewise be a pulsed AC or pulsed DC. The current induced in the induction coil structure 104 will also be proportional to the time rate of change of the magnetic field generated at the site of the induction coil structure 104 by the magnetic field source 112.

In addition, the current induced through the induction coil structure 104 can be modified based on the number of turns 114, the cross sectional area 116, and the length 118 of the induction coil structure 104 of the stent 102, as will be appreciated. In one embodiment, the number of turns 114 of the induction coil structure 104 can be modified based on a configuration of induction coil structure 104.

Figure 2A:
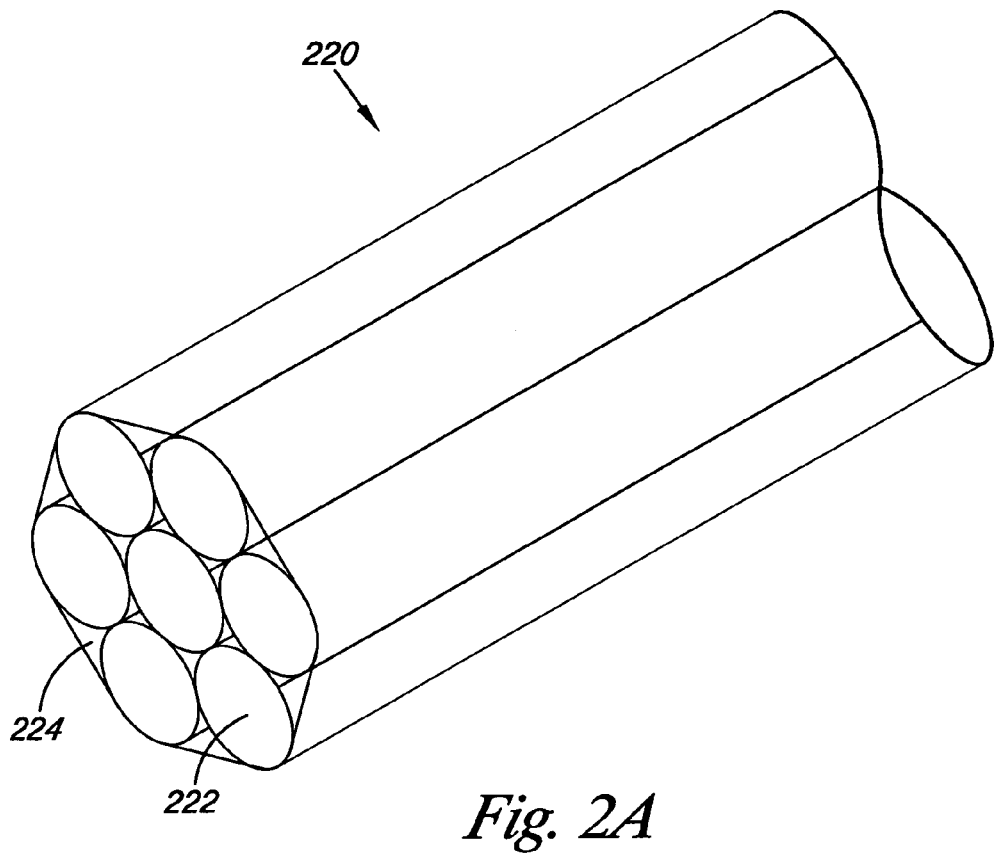
FIGS. 2A and 2B provide illustrations of embodiments of an elongate body used in forming an induction coil structures according to the present disclosure.
Figure 2B:
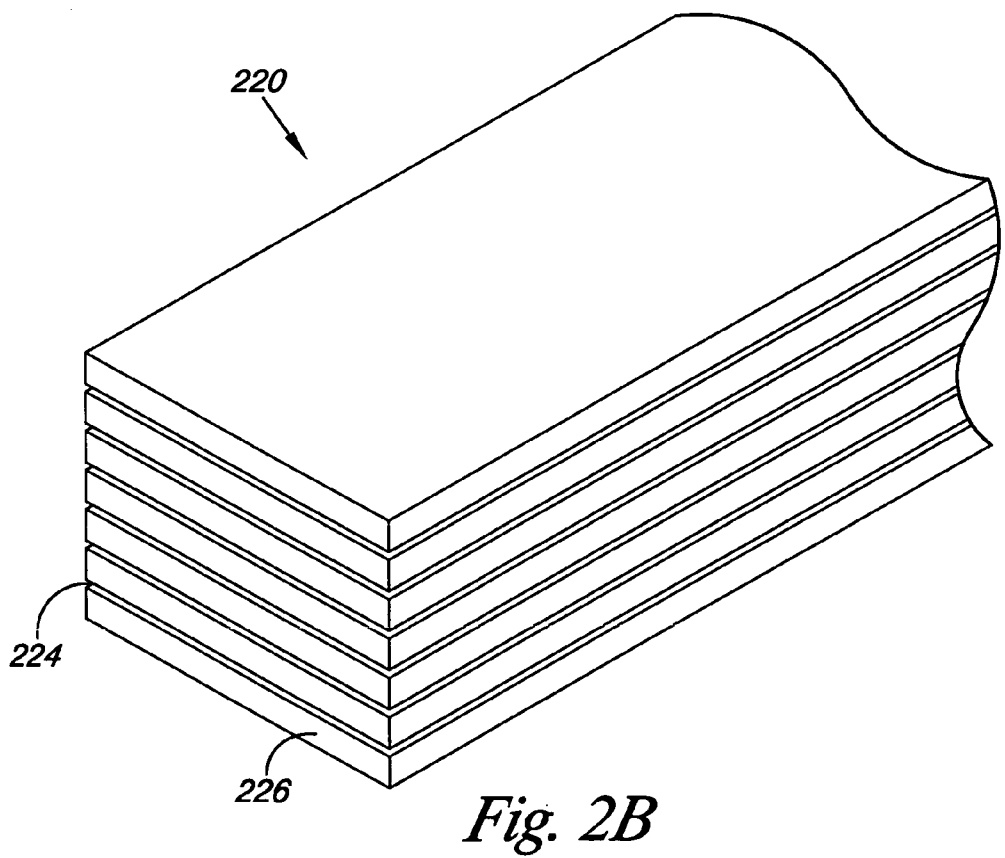

Examples of such configurations according to the present disclosure are illustrated in FIGS. 2A and 2B. FIGS. 2A and 2B provide illustrations of an elongate body 220 used in forming the induction coil structures that have different configurations. As illustrated in FIG. 2A, the elongate body 220 provides a structure with a multi-filar construction. This multi-filar construction allows for the number of turns used in the induction coil structure to be adjusted based on the total number of filar 222 used in the elongate body 220.

As illustrated, each filar 222 can be separated from each adjacent filar 222 with an electrical insulator 224. In one embodiment, the electrical insulator 224 can be provided as a sheath to each filar 222 prior to forming the elongate body 220. Alternatively, the electrical insulator 224 can be provided (e.g., co-extrusion, injection molded) around the adjacent filar 222. As a result, each filar 222 in the illustrated induction coil structure provides an individual induction coil that can be combined with the other induction coils. For example, each of the filar 222 can be electrically coupled in series or in parallel to the control circuit, as will be discussed herein. In one embodiment, the electrical insulator 224 can be a silicone rubber, a polyurethane, or a polyimide. The insulating material may cover the stent in embodiments where at least a portion of the induction coil formed from the elongate body 220 is the stent. In general, the individual turns of wire constituting the induction coil structure 104 are insulated from each other and connected in series to multiply the voltage generated by the coil structure 104. A separate stent structure would not necessarily be insulated, but may be coated with a suitable material that may incorporate a drug or some bio-active agent to promote tissue healing or some therapeutic effect.

FIG. 2B provides an additional illustration of the elongate body 220 having a structure with a laminae construction. The laminae construction allows for the number of turns used in the induction coil structure to be adjusted based on the total number of lamina 226 used in the elongate body 220. As illustrated, each lamina 226 can be separated from each adjacent lamina 226 with the electrical insulator 224. In one embodiment, the electrical insulator 224 can be provided as a layer between each lamina 226. As appreciated, each lamina 226 in the illustrated induction coil structure provides an individual induction coil that can be combined with the other induction coils. For example, each of the lamina 226 can be electrically coupled in series or in parallel to the control circuit, as will be discussed herein.

As will be appreciated, different cross-sectional geometries can be used for the coils in a multi-coil induction coil structure 104. As illustrated herein, the cross-sectional geometries can include circular and rectangular. Other shapes include, but are not limited to, oval and polygonal, among others. In addition, the coil structure 104 can be formed of an elastic alloy which provides radial elasticity. One example of such an elastic alloy is Nitinol. Alternatively, a metal or metal alloy of sufficient strength and elasticity may form the coil structure, including stainless steel, tantalum, or titanium. The coil structure 104 may also contain a good electrical conductor such as copper, silver, or gold to minimize its electrical resistance. Such conductors may constitute a core or cladding within or on a structural material. Alternatively, the coil structure 104 may be comprised of an insulated, conductive metal, while the mechanical structure of stent 102 is comprised of a separate structural material such as 316 stainless steel or nitinol. In addition, one or more of the components of the pacing apparatus 100 can be made radiopaque. For example, one or more portions of the coil structure 104 could be clad with gold or platinum to make the pacing apparatus radiopaque and conductive. Typically, the pacing electrodes 106 and 108 are constructed from a platinum iridium alloy, which is also radiopaque.

The coil structure 104 can further include spacers 127 positioned between the turns of the electrically insulated coils structure 104. In one embodiment, the spacers 127 provide spacing for adjacent turns of the coil structure 104. In an alternative embodiment, spacers 127 are a part of a stent 102 structure to which coil structure 104 is attached. Examples of suitable materials for the spacers 127 include, but are not limited to stainless steel and Nitinol.

Figure 3:
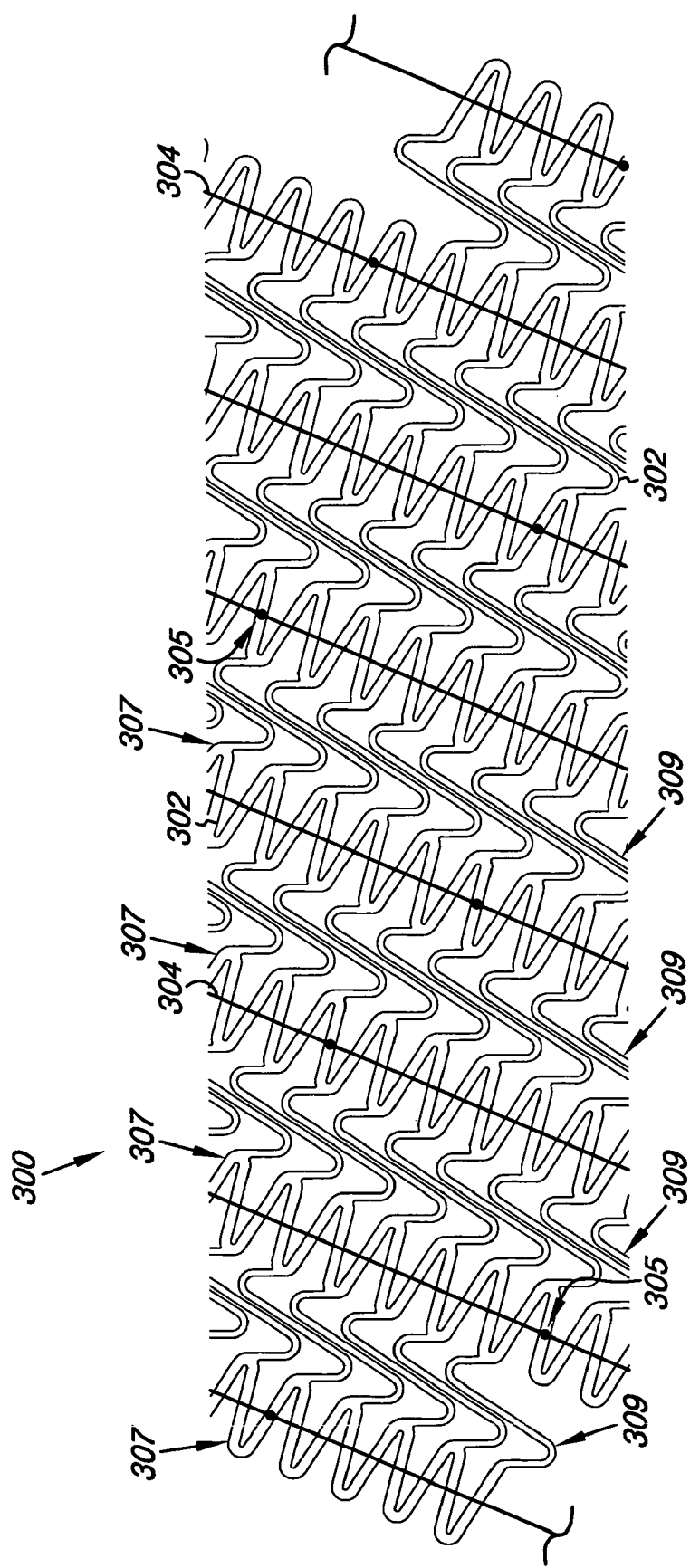
FIG. 3 provides an illustration of one embodiment of a pacing apparatus according to the present disclosure.

FIG. 3 provides an illustration of the pacing apparatus 300 in which the induction coil structure 304 is attached to the structural members of the stent 302. In other words, the stent 302 acts as a scaffold structure that supports the induction coil structure 304 attached thereto. In one embodiment, the induction coil structure 304 can be attached to the structural members of the stent 302 at predetermined locations 305 along both the structural members of the stent 302 and the coil structure 304 in such a way that the coupling of the two structures does not interfere with the normal expansion of the stent 302.

Examples of methods for attaching the induction coil structure 304 to the structural members of the stent 302 at the predetermined locations 305 include physically weaving the induction coil structure 304 through the structural members of the stent 302. In an additional embodiment, the induction coil structure and the stent 302 can be attached through the use of eyelets (i.e., a hole or opening), formed in either the stent 302 and/or the induction coil structure 304, where the eyelets allow the structures to slide past each other through the eyelets. Alternatively, the induction coil structure 304 could be positioned in a frictional fit configuration around the peripheral surface of the structural members of the stent 302. In an additional embodiment, electrically insulating coupling members could be used to join the induction coil structure 304 to the structural members of the stent 302.

In an alternative embodiment, the structural members of the stent 302 could be the induction coil structure, as discussed herein. In other words, the structural members of the stent 302 function as the induction coil as well as the structural component of the stent 302. Specifically, the structural members of the stent 302 could include a conductive member portion 307 and an electrically insulating portion 309. In one embodiment, the conductive member portion 307 has a helical configuration extending along the longitudinal axis of the stent 302, where the electrically insulating portion 309 extend between adjacent turns of the helical configuration.

Figure 4:
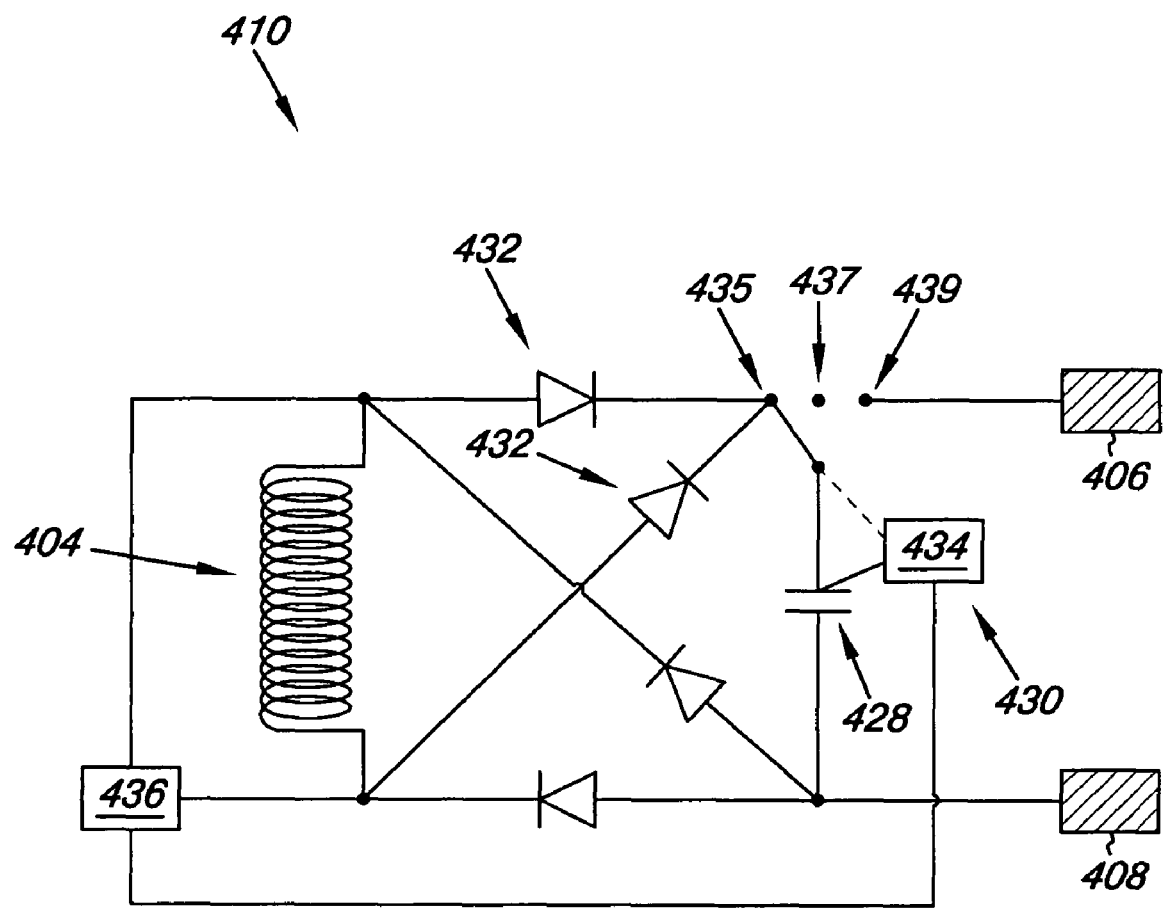
FIG. 4 provides a block diagram illustration of one embodiment of the control circuit according to the present disclosure.

FIG. 4 provides an illustration of the control circuit 110 provided in FIG. 1. As illustrated, the control circuit 410 can include an energy storage device 428, such as a capacitor or a rechargeable battery, and a triggering circuit 430 to deliver the stored electrical current across the first and second electrodes 406 and 408. As illustrated, the energy storage device 428 can be associated with the induction coil structure 404 of the stent and the electrodes 406 and 408, where the energy storage device 428 stores the current generated with the induction coil 404. In one embodiment, the control circuit 410 causes the energy storage device 428 to discharge the current across the electrodes 406 and 408 upon an occurrence of a predetermined event, as will be discussed herein.

In the embodiment of FIG. 4, the control circuit 410 includes a bridge rectifier 432 connected across the induction coil structure 404 to rectify the pulsed AC or pulsed DC that is induced in the induction coil structure 404. The resulting current can be stored on the energy storage device 428. The control circuit 410 further includes a switch 434 that allows for storage of current on the energy storage device 428 and for the subsequent discharge of the current upon receiving a predetermined signal.

For example, the switch 434 includes a first position 435 in which the rectifier 432 produces a rectified output that is imposed across a energy storage device 428. As such, when the switch 434 is in the first position 435, the energy storage device 428 stores the induced electrical current received from the induction coil structure 404.

As the energy storage device 428 charges, the switch 434 monitors the stored current. In one embodiment, the switch 434 acts as a voltage-controlled device that upon reaching a threshold current level moves to a second position 437 to disconnect the energy storage device 428 from the induction coil structure 404. With the switch 434 in the second position 437, the energy storage device 428 can maintain its current until it is ready to be delivered across the electrodes 406 and 408.

In one embodiment, the switch 434 may consist of a solid state switch, such as a field effect transistor, with its gate connected to the output of a voltage comparator that compares the voltage on energy storage device 428 to a reference current. The reference current may be preset, or adjusted remotely after implant via signals from the programmer unit, received by coil 404 and processed by the control circuitry 410. In one embodiment, control circuitry 410 for the pacing apparatus, including the switch 434 can be constructed with components that consume minimal power, for example a complimentary metal-oxide-semiconductor (CMOS). Power for such circuitry can either be derived from a micro-battery contained within the pacing apparatus 400, or derived from current stored on the energy storage device 428.

A narrow band pass filter device 436 can also be connected across the induction coil structure 404, as well as being connected to the switch 434. The band pass filter device 436 can pass a predetermined frequency of a communication signal that is induced in the coil 404. In one embodiment, the predetermined frequency of the communication signal that is passed by the filter device 436 can be unique for the pacing apparatus relative other pacing apparatus. Alternatively, a common communication signal passed by the filter device 436 could be used for two or more of the pacing apparatus relative other pacing apparatus.

When a communication signal having the predetermined frequency is received by the coil 404, the filter 436 passes the induced current to the switch 434. The switch 434 then moves to a third position 439. In the third position 439, the switch 434 connects the energy storage device 428 in series to the electrodes 406 and 408 to allow at least a portion of the current stored on the energy storage device 428 to discharge between the electrodes 406 and 408. In one embodiment, the amount of current discharged between the electrodes 406 and 408 can be sufficient to provide a depolarizing pacing pulse.

After a predetermined interval of time, the switch 434 returns to the first position 435 so that energy storage device 428 may be charged to the selected threshold level. It should be noted that, for sake of clarity, the circuitry 410 illustrated in FIG. 4 provides the components for storing and switching a current. As will be appreciated, additional components may be included in the circuitry 410 to condition the current discharged between the electrodes 406 and 408. Some aspects of the current pulse, for example pulse width and amplitude, may be remotely programmable via encoded signals received through the filter device 436 of the pacing apparatus 400.

In this regard, filter 436 may be a band pass filter with a frequency unique to a pacing apparatus, and the incoming signal may be modulated with programming information. Alternatively, filter 436 may consist of a variety of different types of a demodulator or a decoder that receives analog or digital information induced by the external source in coil 404. The received information may contain a code unique to each pacing apparatus to command discharge of energy storage device 428, along with more elaborate instructions controlling discharge parameters such as threshold voltage for firing, duration, and shape of the discharge pulse, etc.

Figure 5:
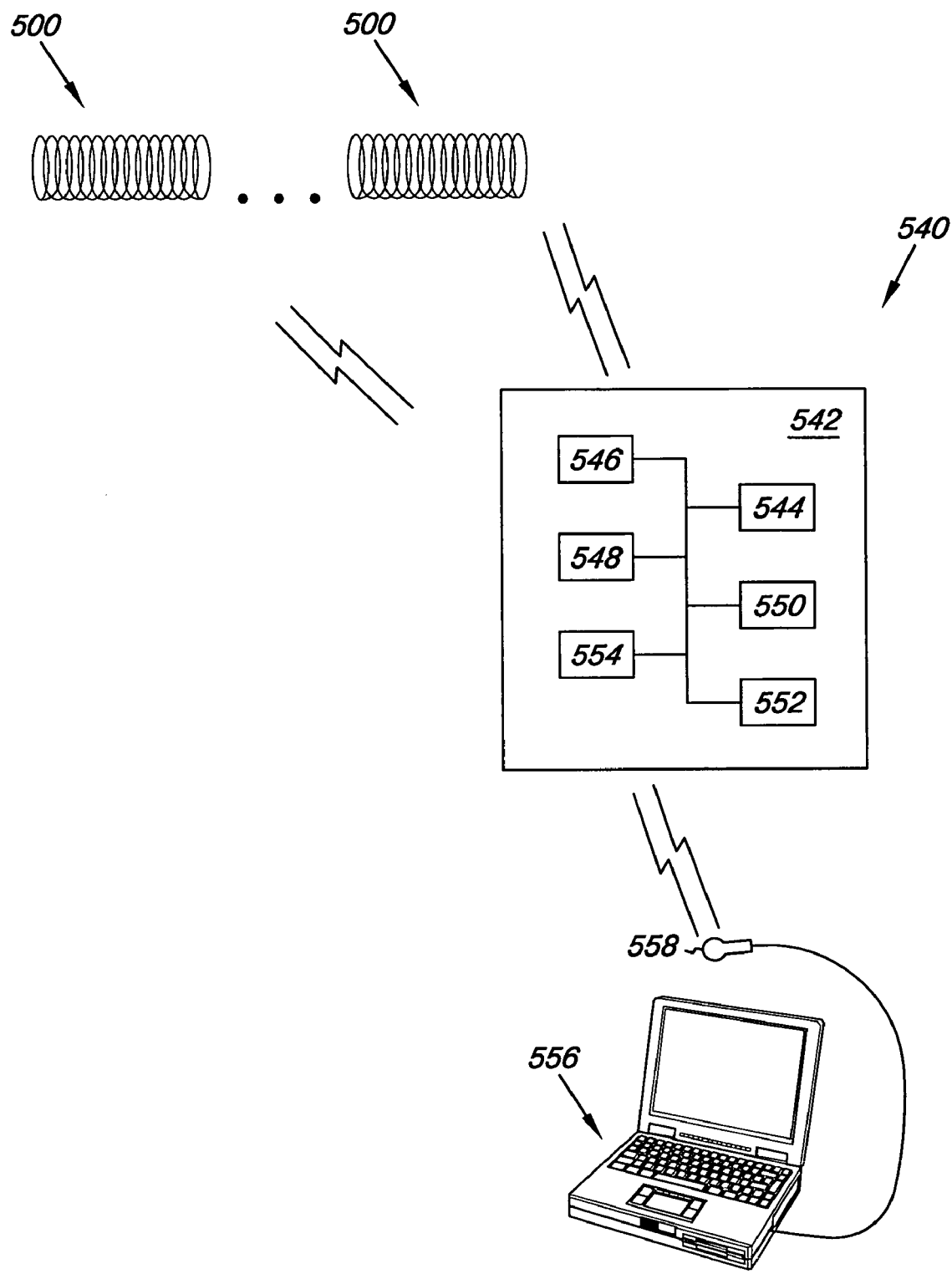
FIG. 5 provides an illustration of one embodiment of a system according to the present disclosure.

FIG. 5 provides an illustration of one embodiment of a system 540 that utilizes the pacing apparatus 500. The system 540 includes the pacing apparatus 500, as discussed herein, a pacing controller 542 and a transmitter 544 that drives an antenna 546 for communication with the pacing apparatus 500. Generally, the pacing controller 542 includes circuitry (signal sensor circuit) to sense and analyze electrical activity of the heart, and to determine if and when a pacing electrical pulse needs to be delivered and which pacing apparatus 500 will deliver the pulse. The sensing capability may be made possible by having sense electrodes included within the physical assembly of the pacing controller 542.

Alternatively, a conventional single or dual lead pacemaker may sense the local cardiac electrocardiogram (ECG) and communicate this information to the controller pacing 542 for use in determination of the timing of pacing apparatus 500. In either case, the pacing apparatus 500 need not be provided with sensing capability, and also the pacing apparatus 500 need not be equipped with the capability of communicating to the pacing controller 542 (for example, to communicate information about sensed electrical events). In alternative embodiments, the pacing apparatus 500 may communicate sensed information to each other and/or to the controller 542.

The transmitter 544, under the control of the pacing controller 542 drives an RF signal onto the antenna 546. The antenna 546 can be configured as a loop antenna formed of a flexible conductive material. Use of the flexible conductive material allows the antenna 546 to be manipulated during implantation into a configuration that achieves the best possible inductive coupling between the antenna 546 and the coils within the pacing apparatus 500. Multiple loop and other antenna configurations are also possible for the antenna 546.

In the embodiment illustrated in FIG. 5, the pacing controller 542 and associated antenna 546 is also shown having battery 548, which may be recharged by receiving RF energy from a source outside the body via antenna 546. The pacing controller 542 can further include ECG sensing electrodes 550 and associated signal sensing circuitry 552 and pacing control circuit 554 for transmitting firing commands to the implanted pacing apparatus 500. The pacing controller 542 can also transmit status information via the antenna 546 to an external programmer 556, receive control instructions from the external programmer 556 and receive power to recharge the battery 548. In alternative embodiments, antenna 546 may receive signals from the pacing apparatus 500 containing information regarding the local ECG at the site of each pacing apparatus, and/or antenna 546 may receive signals from a more conventional implanted pacemaker regarding the ECG signal at the sites of one or more conventional leads implanted on the right side of the heart.

In one embodiment, the transmitter 544 provides both 1) a charging signal to charge the electrical charge storage devices (e.g., the capacitor) contained within the pacing apparatus 500 by inductive coupling, and 2) an information signal, such as a pacing trigger signal, that is communicated to a selected one or more of the pacing apparatus 500, commanding that the pacing apparatus 500 deliver its stored current across the electrodes.

As will be appreciated, each pacing apparatus 500 must generate a required amount of current sufficient to depolarize cardiac tissue (e.g., pace a portion of the heart's ventricle). The energy requirement includes a typical value needed to pace ventricular myocardium, but also includes a margin to account for degradation of contact between the electrodes and tissue over time. It may be assumed that each pacing apparatus 500 may require the maximum pacing threshold energy. This threshold energy may be supplied to the pacing apparatus 500 between heartbeats by an external radio frequency generator (which may also be implanted), or other suitable energy source that may be implanted within the body. Typical values are:

Threshold pacing voltage=2.5 Volts
Typical lead impedance=600 Ohms
Typical pulse duration=0.4 mSec
Derived threshold energy=4 micro-Joules Because radio frequency (RF) fields at frequencies higher than about 100 kHz are attenuated by the body's electrical conductivity, and because electric fields of a variety of frequencies are attenuated within the body, energy transmission through the body may be accomplished via a magnetic field in the range of about 20-200 kHz (or by a magnetic field pulse that contains major frequency components in this range). In one embodiment, the transmission of magnetic fields can be in the range of 20-30 kHz when transmission is through relatively conductive blood and heart muscle.

In one embodiment, the pacing controller 542 and the transmitter 544 may be housed in a single enclosure that is body implantable within a patient. In such a configuration the enclosure device may have an energy source (e.g., an electrochemical battery) that may be either rechargeable or non-rechargeable. In an additional embodiment, the pacing controller 542 and the transmitter 544 may be physically separate components. As an example of such a configuration, the pacing controller 542 may be implantable, for example in the conventional pacemaker configuration, whereas the transmitter 544 (along with the antenna 546) may be adapted to be worn externally, such as in a harness that is worn by the patient. In the latter example, the pacing controller 542 would have its own energy source (e.g., an electrochemical battery), and that energy would not be rechargeable given the relatively small energy requirements of the pacing controller 542 as compared to the energy requirements of the transmitter 544 to be able to electrically charge the pacing apparatus 500. In this case, the pacing controller 542 would sense the local cardiac ECG signal through a conventional pacing lead, and transmit the sensed information to the external programmer 556. Again, transmission of information, as opposed to pacing energy, has a relatively low power requirement, so a conventional pacemaker enclosure and battery would suffice.

The system 540 further includes the external programmer 556 used to communicate with the pacing controller 542. The external programmer 556 may be used to program such parameters as the timing of stimulation pulses in relation to certain sensed electrical activity of the heart, the energy level of stimulation pulses, and the duration and shape of the stimulation pulse, such as the pulse width, pulse shape, and the polarity of the pulses.

In one embodiment, the external programmer 556 includes an antenna 558 to communicate with the pacing controller 542, using, for example, RF signals. The implantable pacing controller 542 is accordingly equipped to communicate with the external programmer 556, using, for example, RF signals. The antenna 546 may be used to provide such communications, or alternatively, the pacing controller 542 may have an additional antenna for external communications with the programmer 556, and in an embodiment where the transmitter 544 and antenna 546 are housed separately from the controller 542, for communications with the transmitter 544.

Figure 6:
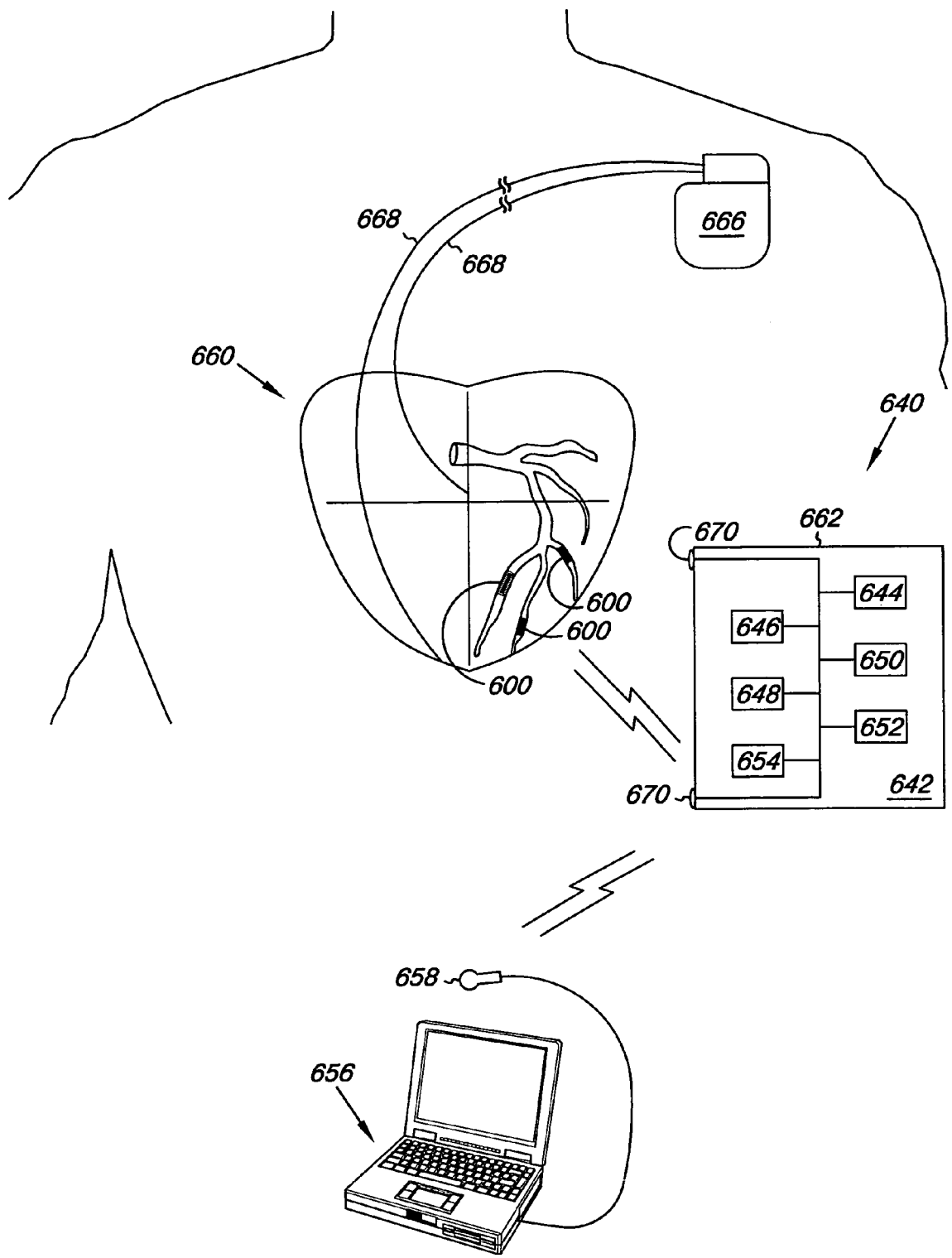
FIG. 6 provides an illustration of one embodiment of a system associated with a heart according to the present disclosure.

FIG. 6 provides an illustration of the system 640 associated with a heart 660. As illustrated, the pacing apparatus 600 are positioned within the coronary vasculature system of the heart 660. The system 640 also includes the pacing controller 642 and transmitter 644 having its antenna 646, all positioned within an implantable housing 662, for communicating, for example, with the pacing apparatus 600.

In one embodiment, the implantable housing 662 containing the pacing controller 642, the transmitter 644 and the antenna 646 can be implanted subcutaneously adjacent the heart 660. The pacing controller 642, the transmitter 644 and the antenna 646 can then be used to charge the pacing apparatus 600, as discussed herein, by providing a RF current field to the induction coil of the pacing apparatus 600. The pacing controller 642 through the transmitter 644 and antenna 646 can then be used to address one or more of the pacing apparatus 600, either individually or in combination, through each of their respective filter devices to trigger pacing.

The system 640 can further include a pulse generator 666 with conductive leads 668 extending from the pulse generator 666 and into one or more portions of the heart 660. In one embodiment, the pulse generator 666 may be used to sense the internal ECG, and may also communicate with the pacing controller 642 as discussed herein.

The pacing apparatus 600 can be controlled to provide depolarization pulses coordinated with predetermined portions of the sensed ECG signal features from the heart 660. ECG signals with which to coordinate the depolarization pulses can be detected using the sensing electrodes 670 on the surface pacing controller 642 to detect the subcutaneous ECG, or it may contain multiple electrodes to provide a more detailed map of electrical activity from the heart. This local ECG signal sensed by the pacing controller 642 may be used to trigger the pacing apparatus 600. In any case, the signals sensed by the pacing controller 642 could be used to monitor ECG signals from the paced heart. In some cases, these ECG signals, or other physiologic sensor input signals, may be used to adjust or adapt the timing of firing of the pacing apparatus 600.

In addition, ECG signals with which to coordinate the depolarization pulses can be sensed from the pulse generator 666 that is in communication with the pacing controller 642 through either an RF link or direct hard wire connection. This may be desirable in patients who already have a conventional pacemaker, or when local ECG data from the conventional atrial or right ventricular apex pacing sites are desired to coordinate the timing of firing of the pacing apparatus 600.

Finally, the pacing apparatus 600 could themselves transmit information to pacing controller 642 concerning the local bi-polar ECG measured at their sites. Alternatively, the pacing apparatus 600 could sense the local ECG and discharge based upon this local data, with no firing instructions from the pacing controller 642 required. In an additional embodiment, the pacing apparatus 600 could transmit information from pacing apparatus 600 to the pacing controller 642 concerning local ECG and the onset of their discharge. All of the above embodiments, or a subset, may be implemented according to the present embodiments of the disclosure.

As will be appreciated, when two or more pacing apparatus 600 are used, the pacing controller 642 can be programmed to cause pacing pulses to be delivered to the heart 660 via the pacing apparatus 600 so as to coordinate the contraction of the chamber of the heart (e.g., coordinate the contraction of the ventricles of the heart). In addition, one or more of the pacing apparatus 600 may be programmed not to discharge. For example, an array of pacing apparatus 600 may be implanted, but only a subset may be programmed to receive firing commands from the controller 642.

For the embodiment of FIG. 6, and other similar embodiments, the pacing controller 642 and associated antenna 646 could first be implanted subcutaneously in a designed location. The pacing controller 642 may then be programmed by delivering telemetric signals through the skin using the programmer 656, although this programming may also be done, at least in part, before implantation. One of the adjustable parameters is the timing of firing of each pacing apparatus 600, determined by a time at which a short burst of current at the frequency for the particular pacing apparatus 600 is delivered to the antenna 646.

Figure 7C:
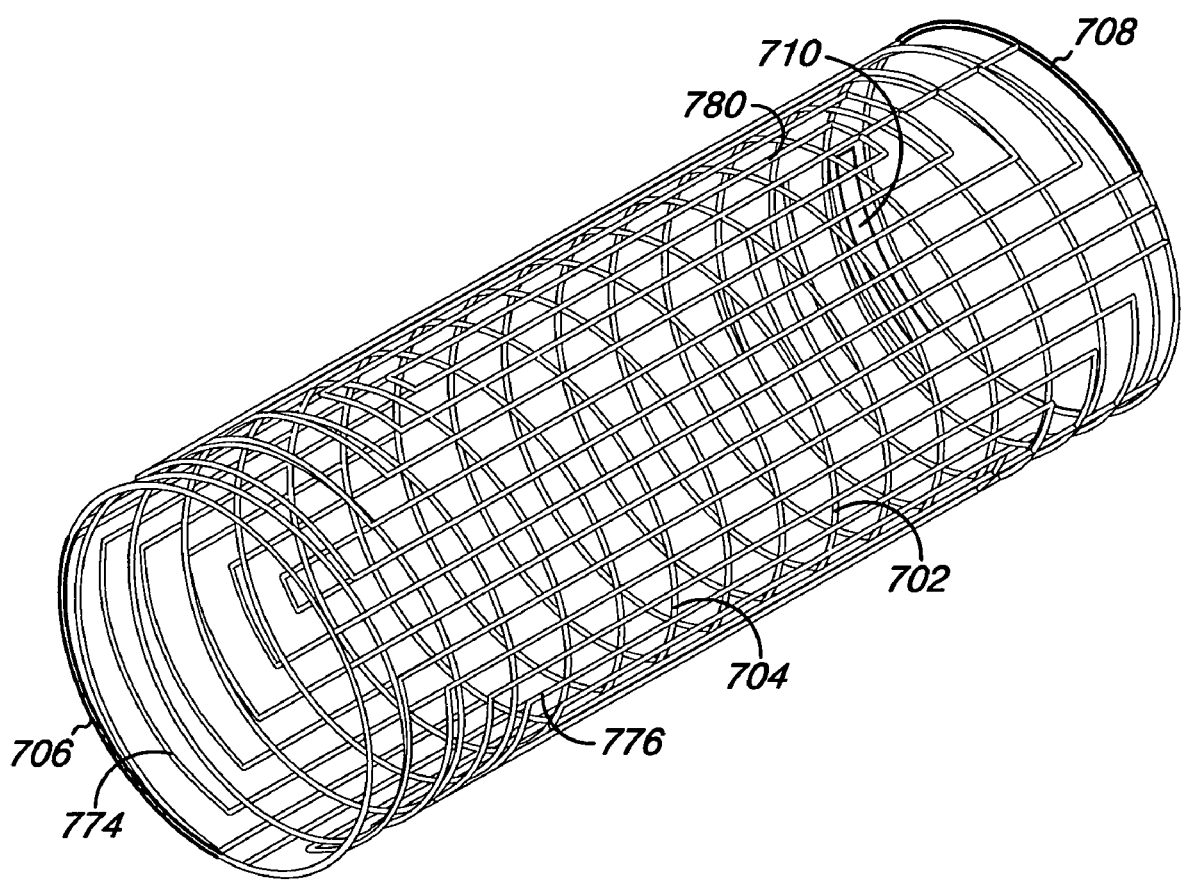

FIGS. 7A-7C provide illustrations of additional embodiments for the pacing apparatus 700 according to the present disclosure. FIG. 7A provides an exploded view of the pacing apparatus 700 that includes the induction coil 704, as discussed herein, a second induction coil 774 and a third induction coil 776.

As discussed herein, the induction coil structure 704 can extend circumferentially along a longitudinal axis of the stent 702. As illustrated, the second induction coil 774 and the third induction coil 776 partially encircle and extend longitudinally along the longitudinal axis of the stent 702. As will be appreciated, the second induction coil 774 and/or the third induction coil 776 can extend up to, and beyond, the length of the adjacent induction coil structure 704. FIG. 7A provides an illustration in which the second induction coil 774 and the third induction coil 776 are approximately the same length as the induction coil structure 704.

The second induction coil 774 and the third induction coil 776 are physically and electrically associated with the stent 702. Both the second induction coil 774 and/or the third induction coil 776 can have structural and electrical configurations relative the control circuitry 710 and the first and second electrodes 706 and 708 as discussed herein for the induction coil 704. So, for example, the second induction coil 774 and/or the third induction coil 776 can inductively couple to a magnetic field source impinging on the pacing apparatus 700.

In one embodiment, the induction coils 704, 774 and 776 are electrically insulated from each other while being physically coupled together in the stent 702 configuration. In one embodiment, the induction coils 704, 774 and 776 are physically coupled in such a way that the relative position of the coils 704, 774 and 776 is essentially maintained as the stent 702 is deployed (e.g., expands) in the coronary vascular system of the heart.

In another embodiment, one or more of the induction coils 704, 774, and 776 may have an electrical function, but not contribute to the stent structural support. In this case, the induction coils may be constructed from flexible, insulated wire, or other flexible materials that deform when compressed, and open when the stent is expanded to the configurations shown in FIG. 7C. This embodiment is similar to the embodiment illustrated in FIG. 3, discussed herein.

As illustrated in FIGS. 7A and 7B, the second induction coil 774 and the third induction coil 776 can be positioned radially relative the longitudinal axis of the stent 702, where the induction coils 704, 774 and 776 are positioned orthogonally relative each other. This configuration allows for inductive coupling to a magnetic field source impinging on the pacing apparatus 700 from more than one direction.

The control circuit 710 further includes a bridge rectifier circuit coupled to the induction coil structure 704, the second induction coil 774 and the third induction coil 776 to rectify current generated with the coil structures 704, 774 and 776. FIGS. 7A and 7B provide an illustration in which the control circuit 710 is positioned within the lumen of the stent 702. In addition, FIG. 7A illustrates an embodiment in which the first electrode 706 extends from a first end of the induction coil structure of the stent 702, and the second electrode 708 extends from a second end opposite the first end of the induction coil structure 704 of the stent 702.

FIG. 7C provides an additional embodiment of the pacing apparatus 700. As illustrated, the pacing apparatus 700 includes coil structures 704, the second induction coil 774 and the third induction coil 776. In addition, the pacing apparatus 700 includes a fourth induction coil 780. Each of the second, third, and fourth induction coils 774, 776 and 780 can extend circumferentially along a longitudinal axis of the stent 702 so as to partially encircle the stent 702. The second, third, and fourth induction coils 774, 776 and 780 can also be physically and electrically associated with the stent 702, with structural and electrical configurations relative the control circuitry 710 and the electrodes 706 and 708 as discussed herein for the induction coil 704 (e.g., connected in series or parallel). So, the second induction coil 774, the third induction coil 776 and/or the fourth induction coil 780 can inductively couple to a magnetic field source impinging on the pacing apparatus 700.

In one embodiment, the induction coils 704, 774, 776 and 780 are electrically insulated from each other while being physically coupled together in the stent 702 configuration. In one embodiment, the induction coils 704, 774, 776 and 780 are physically coupled in such a way that the relative position of the coils 704, 774, 776 and 780 are essentially maintained as the stent 702 is deployed (e.g., expands) in the coronary vascular system of the heart.

As illustrated in FIG. 7C, the second induction coil 774 and the third induction coil 776 and the fourth induction coil 780 can be positioned radially relative the longitudinal axis of the stent 702, where the induction coils 774, 776 and 780 are positioned so as to surround the induction coil 704. As illustrated, each of the induction coils 774, 776 and 780 are positioned over about a third of the peripheral surface of the induction coil 704. In other words, the induction coils 774, 776 and 780 are circumferentially arranged around the coil 704. This configuration allows for inductive coupling to a magnetic field source impinging on the pacing apparatus 700 from more than one direction. In other words, the pacing apparatus 700 can collect magnetic flux in each of three orthogonal directions, so that maximum flux is collected independent of the orientation of the incident magnetic field. In general, a minimum of three induction coils oriented in three orthogonal directions are required to couple magnetic fields coming from more than one direction.

The control circuit 710 further includes half wave or full wave bridge rectifier circuits coupled to the induction coil structure 704, the second induction coil 774, the third induction coil 776, and the fourth induction coil 780 to rectify current generated with the coil structures 704, 774, 776 and 780. As will be appreciated, when induction coils (e.g., 774, 776, and 780) are positioned on opposite sides of the stent 702 they can be wound in the same manner and connected in series to multiply induced voltage. FIG. 7C further provides an illustration in which the electrodes 706 and 708 partially encircle the stent 702.

Figure 8A:
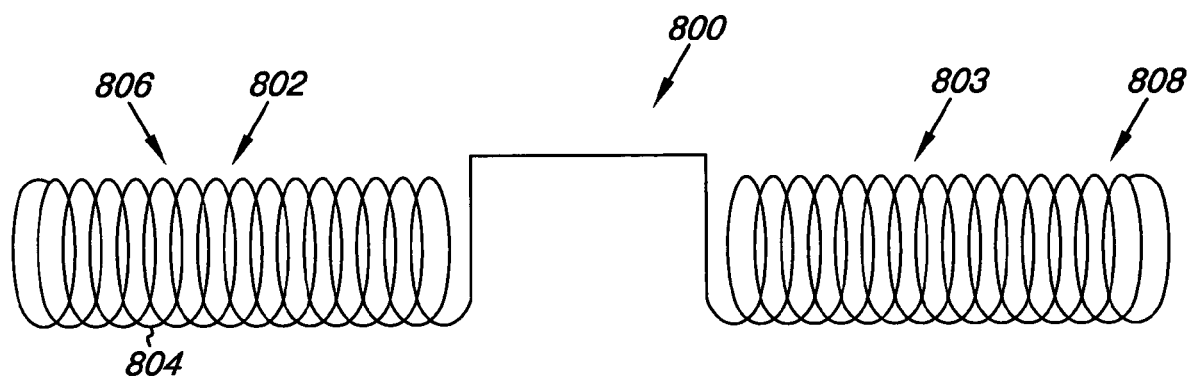
FIGS. 8A-8C provide illustrations of additional embodiments of the pacing apparatus according to the present disclosure.
Figure 8B:
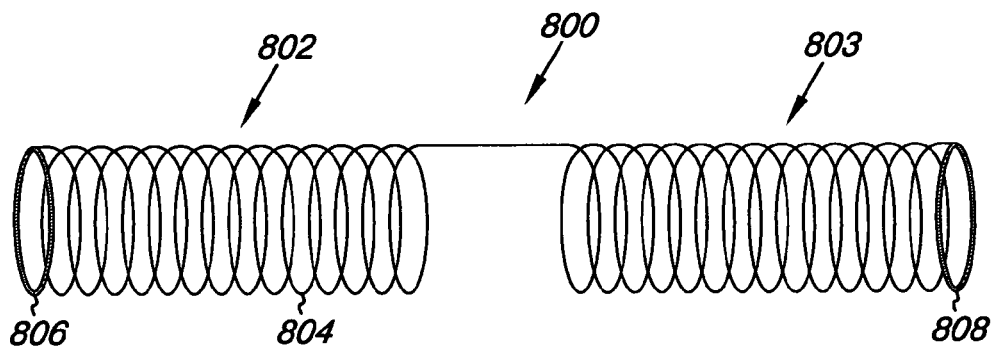
Figure 8C:
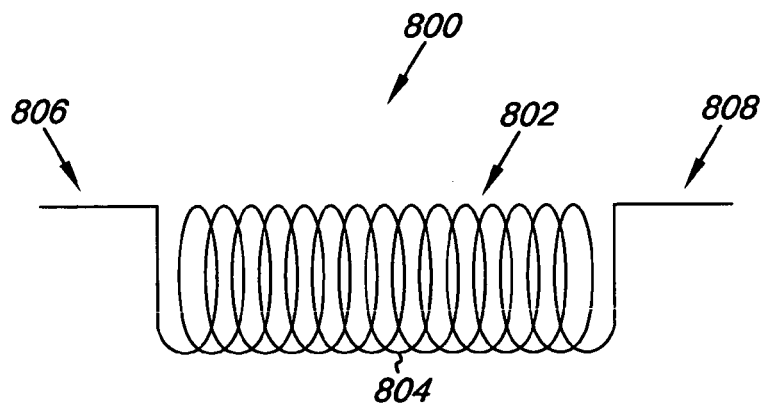

FIGS. 8A-8C provide illustrations of additional embodiments of the pacing apparatus 800 according to the present disclosure. As illustrated, the pacing apparatus 800 has been simplified by the omission of the control circuit discussed herein. That is, the pacing apparatus 800 consists of at least one induction coil structure 804 and the associated electrodes 806 and 808. As illustrated in FIG. 8A, the pacing apparatus includes a second stent 803 with an induction coil structure, as discussed herein, that conductively joins the first stent 802. The first and second stents 802 and 803 can then be used to generate the current that is discharged between the electrodes 806 and 808. FIG. 8B provides an illustration that includes the electrodes 806 and 808 in the form of first and second ring electrodes that at least partially encircles the stent 802 and the second stent 803, respectively.

For these embodiments, a magnetic field pulse induces a voltage pulse in at least one induction coil structure 804, and the induced voltage directly discharges into tissue. If all pacing apparatus 800 are the same, pacing of all pacing apparatus 800 can occur simultaneously. However, the rise time of the induced voltage can be adjusted by adjustment of the coil parameter number of turns, core permeability, and adjustment of a resistor in series with the coil. Thus, a collection of pacing apparatus 800 having varying rise times can be used to synchronize the firing sequence of the pacing apparatus 800. So, the pacing controller may be used to sense a local ECG and provide a current to the pacing apparatus 800, with the precise time of firing determined by the electrical properties of each pacing apparatus 800.

The procedure for implanting pacing apparatus of the present application is similar to that used for vascular stents that are employed to enlarge a restricted vein or artery. Such vascular stents have a generally tubular design that initially is collapsed to a relatively small diameter enabling them to pass freely through an artery or vein of a patient. For example, an inflatable balloon positioned at or near the end of a catheter can be inserted into the pacing apparatus of the present disclosure in its collapsed, or reduced diameter, configuration. That assembly then is inserted through an incision in a vein or artery near the skin of a patient and moved through the vascular system to the appropriate location adjacent the heart.

In an alternative embodiment, pacing apparatus delivery can include use of a self expanding material for the structural aspect of the pacing apparatus. The pacing apparatus can initially be collapsed and inserted into a sheath near the distal end of a catheter. After insertion into an artery or vein at the target location, the sheath is pulled back, and the pacing apparatus expands automatically to its expanded configuration adjacent the vessel wall. Nitinol is a typical self-expanding material that could be used for the pacing apparatus. Flexible induction coils could be attached to the nitinol frame, or the self expanding stent material could serve dual support and electrical functions if it takes the form of an induction coil.

The pacing apparatus can be ultimately positioned in a cardiac vein and/or cardiac artery adjacent to a section of the heart muscle where stimulation should be applied. For example, the pacing apparatus can be positioned in a distal cardiac vein through the coronary sinus to pace the left ventricular free wall of the heart. Once in position, the balloon of the catheter is inflated to expand the pacing apparatus to embed the electrodes of the pacing apparatus in the vessel wall. As will be appreciated, the tubular design of the stent of the pacing apparatus allows blood to flow relatively unimpeded through the device. The balloon is deflated, the catheter is removed from the patient, and the incision is closed. The pacing apparatus remains in the vessel without a wire connecting the electrodes to a pacing device.

Once implanted, one or more of the pacing apparatus may be charged and fired to observe the coordination of the cardiac contraction. The physician can adjust the pacing parameters (e.g., the timing) of pacing apparatus firing by programming the pacing controller. When satisfied with the local and pacing controller electrograms, the catheter may be removed, and a new delivery mechanism containing the next pacing apparatus may be inserted and navigated to the next pacing site. Because pacing apparatus can be fired in a predetermined order, or not fired at all, a physician may deliver the pacing apparatus in a desired order.

When the heart is deemed to be beating in synchrony, no further pacing apparatus need be implanted. Alternatively, if it has been determined that the pacing apparatus are small enough that they do not substantially impair local tissue function, then an array of pacing apparatus may be delivered to the coronary vasculature, and the physician can program a subset of pacing apparatus to fire in a sequence that best optimizes the pumping efficiency of the heart. Ejection fraction and cardiac output may be measured to determine pumping efficiency. On a given heartbeat, some or all of the pacing apparatus would fire. The pacing controller may be programmed to sequentially fire pacing apparatus, or some pacing apparatus may fire simultaneously. Wireless pacing apparatus such as those described in the US patent application entitled "Leadless Cardiac Stimulation Systems" (Ser. No. 10/971, 550 filed on Oct. 20, 2004, the entire contents of which is hereby incorporated by reference) may be attached to the wall of the heart or injected into the wall of the heart at sites not accessible via the vascular system of the heart.

When applied to the treatment of atrial fibrillation, the catheter used to deliver the pacing apparatus can be inserted through the inferior or superior vena cava and into the right atrium of the heart. In a standard procedure, the catheter is inserted through the fossa ovalis cordis in the atrial septum to gain access to the left atrium from the right. The catheter can then be inserted into one of the four or more pulmonary veins emptying into the left atrium, and the pacing apparatus is delivered into the pulmonary vein near its opening in the left atrium. The pacing apparatus can then be paced from the external programmer and the heart rhythm is assessed. If the atrial fibrillation has terminated, the procedure may be finished. If not, additional pacing apparatus may be placed in other of the pulmonary veins until all veins have received pacing apparatus that are simultaneously paced or paced in timed sequence determined by the operator. If atrial fibrillation has not terminated at this point, pacing apparatus may be placed in other veins in or around the left or right atrium, such as the coronary sinus vein. If atrial fibrillation still persists, wireless pacing apparatus such as those described in the US patent application entitled "Leadless Cardiac Stimulation Systems" (Ser. No. 10/971,550 filed on Oct. 20, 2004, the entire contents of which is hereby incorporated by reference) may be attached to the wall of the heart or injected into the wall of the heart at sites not accessible via the vascular system of the heart. Alternative therapies, such as tissue ablation, may be applied if an arrhythmia persists after the completion of pacing apparatus implantation.

Figure 9:
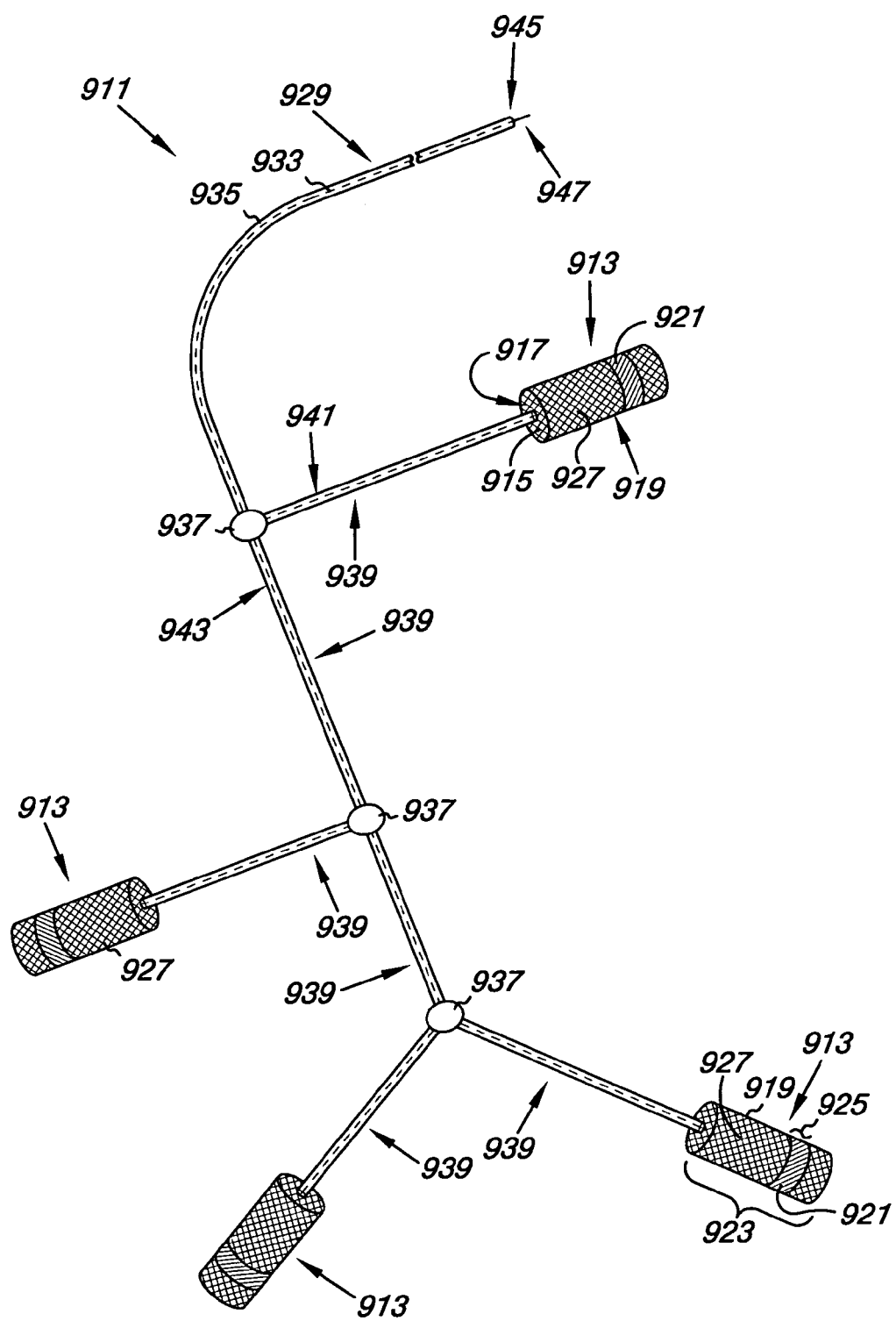
FIG. 9 provides an illustration of an additional embodiment of a pacing apparatus according to the present disclosure.

Referring to FIG. 9, there is shown an additional embodiment of a pacing apparatus 911 according to the present disclosure. As illustrated, the pacing apparatus 911 includes a vascular stent 913 having a first surface 915 defining a lumen 917. The vascular stent 913 further includes a second surface 919 opposite the first surface 915, where the second surface 919 has an electrically conductive portion 921. In one embodiment, the electrically conductive portion 921 can be used as an electrode (uni-polar or bi-polar electrode) in delivering a current to a heart.

As illustrated, the electrically conductive portion 921 is positioned to face radially away from lumen 917 of stent 913.

The second surface 919 also defines a first area 923 (i.e., the entire area of the second surface 919), where the electrically conductive portion 921 defines a second area 925 that is less than the first area 923. In one embodiment, the first area 923 of the second surface 919 can be covered with an electrically insulating layer 927, where the areas of the second surface 919 not covered by the electrically insulating layer 927 can provide the second area 925 of the stent 913. In one embodiment, the electrically insulating layer 927 can be a silicone rubber, a polyurethane, a polyimide, paraline or other biocompatible, electrically insulating material.

In an alternative embodiment, the electrically conductive portion 921 of the pacing apparatus 911 can be in the form of a ring electrode that at least partially encircles the elongate body of the pacing apparatus 911. As will be appreciated, other structures and/or shapes are also possible for the electrically conductive portion 915 of the pacing apparatus 911. For example, the electrically conductive portion 915 could have a partial ring, spherical, or partial spherical structure. Other shapes are also possible.

The first surface 915 also includes the electrically insulating layer 927 to prevent electrical current from being conducted through the blood within the lumen 917 of the stent 913. In one embodiment, the electrically conductive portion 921 of the stent 913 is positioned in this fashion so as to minimize its exposure to blood that will be flowing through the lumen of the stent 913 and to maximize the exposure of the adjacent myocardial tissue to the electrically conductive portion 921 once positioned within the coronary vasculature of the heart. In one embodiment, the electrically insulating layer 927 can be a silicone rubber, a polyurethane, a polyimide, or paraline.

As illustrated in FIG. 9, the pacing apparatus 911 can include two or more stents 913 (e.g., a first stent, a second stent, etc.), where each stent 913 can be physically and electrically coupled to a portion of the electrically insulated lead 929. The electrically insulted lead 929 includes a conductor 933 that extends within an insulating sheath 935, where the conductor 933 physically and electrically connects to the electrically conductive portion 921 of the pacing apparatus 911.

As shown, the electrically insulated lead 929 divides at one or more of a branch node 937 into two or more branch leads 939 that extend either to another stent 913 or to another branch node 937. In this way, a network of two or more stents 913, each having their own electrically insulated lead and branch nodes 937 can be formed. For example, as illustrated in FIG. 9, there is shown a first branch lead 941 and second branch lead 943 that extend from the branch node 937. The first branch lead 941 then couples to the electrically conductive portion 921 of the stent 913, while the second branch lead 941 couples to the electrically conductive portion 921 of a second of the stent 913. This general pattern can be repeated using a number of branch nodes 937, branch leads 939 and stents 913 to form the network of the pacing apparatus 911.

In one embodiment, the branch node 937 can include at least one bifurcation of the electrically insulated lead 929 into the branch leads 939. In an additional embodiment, the branch node 937 can include a circuit to direct a predetermined portion of the electrical current through a predetermined branch lead. For example, the circuit contained within the branch node 937 can include a switch, a capacitor, a transistor, a resistor, a diode, and/or an inductor, or other discrete device for regulating the amount of current, the timing of the current delivery, and to which branch lead the current is directed. As will be appreciated, the forgoing is given as non-limiting examples of the parameters for the electrical current that can be modified at the branch node 937.

In general, the nodes 937 are addressed by a central controller. The central controller may be contained in a pacemaker connected to lead 947, or contained in an external programmer that communicates with node 937 or with one of the electrically conductive portion 921 attached to node 937 or from coil 1051 via a RF communications link. Communications can be coded, where each node has its own unique code for receiving communications. The nodes 937 may also receive local ECG signals sensed using the electrically conductive portion 921 of the vascular stent 913. When node 937 receives a signal to deliver pacing energy to the electrically conductive portion 921, a field effect transistor (FET) switch within node 937 opens, directing pacing energy from the power source 1051 or 1163 through lead 947 into lead 941 to the electrically conductive portion 921. Node 937 may also contain a programmable microprocessor that allows the decision to fire the electrically conductive portion 921 to be based in part upon the signal sensed from the electrically conductive portion 921 prior to firing. For example, if depolarization has already occurred at the site of the electrically conductive portion 921 when the firing command is given, node 937 would not open the FET switch connecting lead 947 to lead 941.

In one embodiment of FIG. 9, electrical connectors are mounted to the vascular stent 913 with a single connector attached to each stent. To deliver this embodiment to the vasculature, all stents are first delivered individually to their sites in the vascular tree via stent delivery catheters. A catheter carrying leads 939 and nodes 937 is then advanced into the vascular system, and the leads are plugged into the stents. The most distal node would be connected first. A sheath on the lead delivery catheter would then be pulled back to expose the second lead, which would be plugged into the second most distal stent, etc., until all stent electrodes have been connected to their respective leads.

In a second embodiment of FIG. 9, the stents are delivered one at a time, each stent having a trailing lead that deploys when the catheter is withdrawn. A second catheter is then introduced that contains the central backbone lead 933 and nodes 937. A special tool on the second catheter is used to plug leads 939 extending back from each stent into the nodes 937, progressing proximally from the most distal node until all nodes are connected.

The pacing apparatus 911 further includes an electrically insulated lead 929 having a first end 945 with a connector 947 that can releasably couple the pacing apparatus 911 to a source of electrical current. In one embodiment, the connector 947 can include a terminal pin that can releasably connect to an implantable pulse generator (e.g., a pacemaker unit) that is the source of the electrical current. In an alternative embodiment, the connector 947 can be configured to couple to an induction coil structure that is the source of the electrical current.

Figure 10:
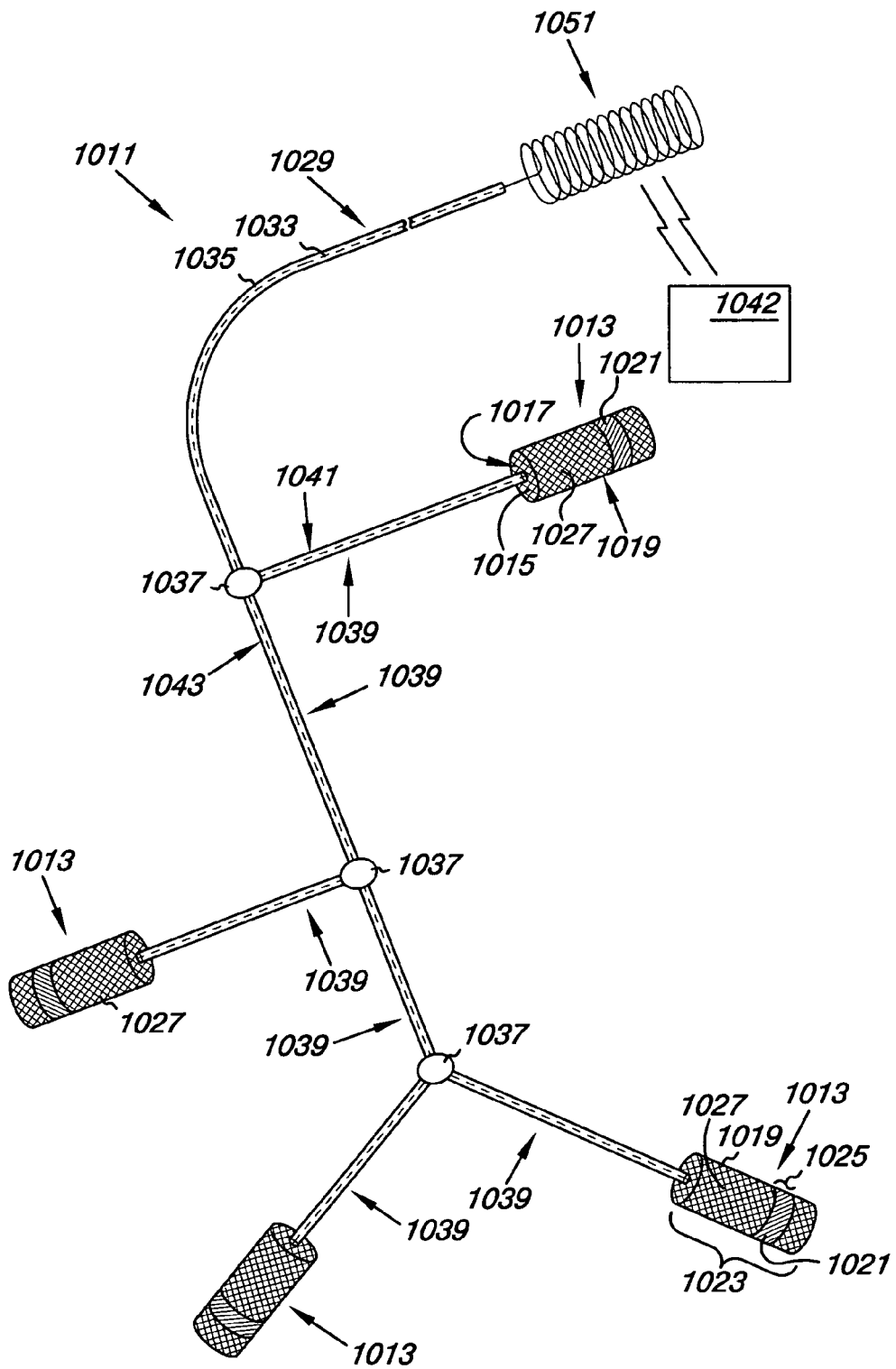
FIG. 10 provides an illustration of an embodiment of the pacing apparatus coupled to an induction coil structure according to the present disclosure.

For example, FIG. 10 provides an illustration of the pacing apparatus 1011 coupled to an induction coil structure 1051. As discussed herein, the induction coil structure 1051 can have a variety of configurations that allow for the generation of an electrical current that can be delivered to the electrically conductive portion of the vascular stent 1013 during a predetermined portion of the cardiac signal. In one embodiment, the induction coil structure 1051 can be positioned within the inferior vena cava or pulmonary trunk. As will be appreciated, two or more of the induction coil structure 1051 may be used in the pacing apparatus 1011. It will also be appreciated that coil structures may contain a means to store impending RF energy, such as a rechargeable battery or capacitor, and may also contain micro-electronics, including but not limited to a microprocessor with externally programmable memory circuitry for communicating with an external programmer.

As will be appreciated, the pacing controller 1042 may contain a signal sensor circuit to sense and analyze a cardiac signal sensed from the electrical activity of the heart. The pacing controller 1042, through the transmitter unit, can then emit electromagnetic impulses to cause the induction coil 1051 to generate the electrical current for delivery during a predetermined portion of the cardiac signal. In one embodiment, the timing of the delivery of the currents across the stents 1013 can be determined in part by the electrical potential sensed at the site of each stent electrode, or at the nodes 1037. For example, if electrical depolarization is sensed at the site of the electrode, then node 1037 would not energize that electrode. Coil 1051 would be delivered by a stent delivery catheter as described herein, and subsequently be connected to node 1037.

Figure 11:
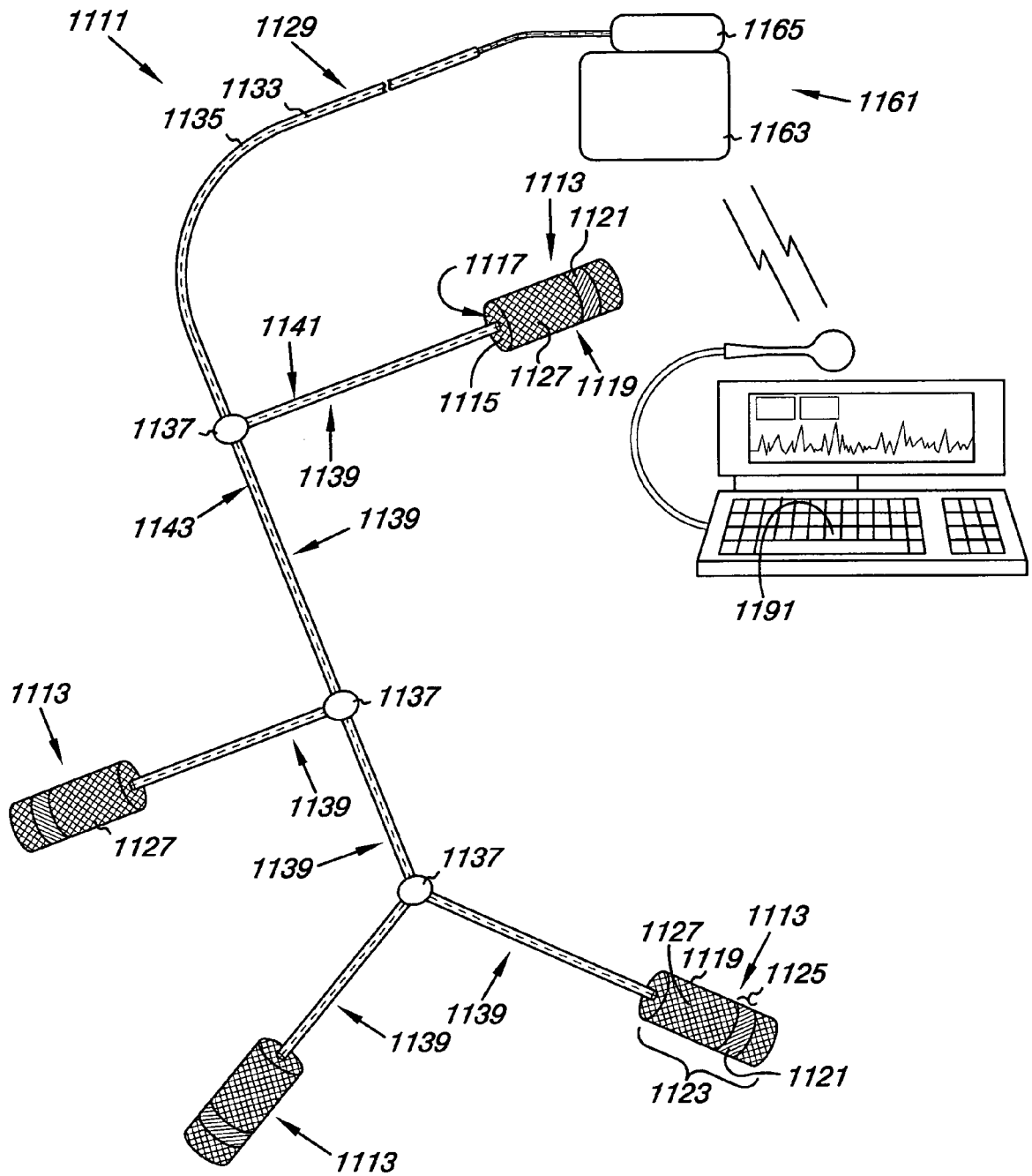
FIG. 11 provides an illustration of an embodiment of the pacing apparatus coupled to an implantable pulse generator according to the present disclosure.

FIG. 11 illustrates an additional embodiment in which the pacing apparatus 1111 can be releasably coupled to an implantable pulse generator 1161. As illustrated, the pacing apparatus 1111 can be releasably coupled to the pulse generator 1161 so as to couple the stents 1113 to the electronic circuitry within the pulse generator 1161. This allows for cardiac signals to be sensed from and electrical energy pulses to be delivered to the heart via the stents 1113.

Different pacing needs of the patient can be met by adjusting the programming of the pulse generator 1161 and by the location in which the stents 1113 of the pacing apparatus 1111 are implanted. In one embodiment, the stents 1113 can be implanted in the coronary vasculature adjacent the cardiac region in need of pacing. For example, the proximal stent electrodes may be placed in the coronary sinus vein accessed via the right atrium to pace tissues of the right and left atria, and the distal stent electrodes would then be placed in veins that branch from the coronary sinus vein to pace tissues of the right and left ventricles. The stents 1113, through the use of a combination of the implantable pulse generator 1161 and the branch nodes 1137, can be used to sense cardiac signals and to deliver pacing pulses to the cardiac tissue.

As discussed herein, these pacing pulses delivered to the heart can be used in a cardiac resynchronization therapy. As will be appreciated, different combinations of the stents 1113 and the housing of the pulse generator 1161 can be used in both sensing cardiac signals from and delivering pacing pulses to the heart (e.g., bi-polar combinations of stents 1113 and/or housing, and/or uni-polar sensing and pacing with the stents 1113 and the housing).

The pulse generator 1161 includes a signal sensor circuit coupled to the electrically conductive portion 1121 of the vascular stent 1113 to sense a cardiac signal. In one embodiment, the signal sensor circuit is a programmable microprocessor-based system, with a microprocessor and a memory circuit that contains parameters for various pacing and sensing modes and store data indicative of cardiac signals received by the signal sensor circuit. The signal sensor circuit also includes sense amplifiers to facilitate one or more cardiac signals to be sensed through the use of the pacing apparatus 1111.

The pulse generator 1161 also includes a pulse generator circuit coupled to the signal sensor circuit to generate a predetermined pacing current delivered to the electrically conductive portion 1121 of each of the vascular stents 1113 during a predetermined portion of the cardiac signal, so that each stent electrode is paced at the appropriate time in the cardiac cycle. The pulse generator 1161 includes a housing 1163 that encases and hermetically seals the circuitry and a power source (e.g., an electrochemical battery) suitable for implanting in a human body. In one embodiment, the housing 1163 can be coupled to the circuitry described herein to act as a pole for sensing and pacing of the heart. In one embodiment, the housing 1163 is made of titanium; however, other biocompatible housing materials as are known in the art may be used. A connector block 1065 is additionally attached to the housing 1161 to allow for the physical and the electrical attachment of the pacing apparatus 1111 via its connector.

The pulse generator 1161 can further include electronic communication circuitry coupled to the signal sensor circuit and the pulse generator circuit to allow the pulse generator 1161 to communicate with an external programmer 1191. In one embodiment, the electronic communication circuitry includes a data receiver and a data transmitter to send, receive, and transmit signals and cardiac data to and from the external programmer 1191. In one embodiment, the data receiver and the data transmitter include a wire loop antenna to establish a RF telemetric link to receive and transmit signals and data to and from the external programmer 1191.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
   an intravascularly-deliverable wireless stent electrode assembly comprising:
     an expandable mechanical structure;
     a plurality of at least partially overlapping induction coils attached to the expandable mechanical structure, and electrically insulated from the expandable mechanical structure, and from each other, each induction coil including an elongate body positioned along a long axis of the stent and configured to wirelessly receive magnetically-coupled energy;
     one or more electrostimulation electrodes electrically configured to deliver at least some of the received magnetically-coupled energy as an electrostimulation to one or more tissue sites;
     wherein the plurality of induction coils are deformable and configured to open when the mechanical structure is expanded;
     wherein at least two of the plurality of induction coils are positioned at least partially orthogonally relative to each other; and
     wherein each elongate body includes a laminar construction and is configured to be electrically insulated from one or more at least partially overlapping adjacent laminae, and electrically insulated from the expandable mechanical structure.

2. The apparatus of claim 1, comprising:
   a control circuit comprising an energy storage device electrically connected to the induction coil, the energy storage device configured to store at least some of the magnetically-coupled energy, the control circuit positioned at an end of the wireless stent electrode assembly and configured to provide a signal in coordination with one or more predetermined events and, in response to the signal, the one or more electrostimulation electrodes are configured to deliver the at least some of the stored magnetically-coupled energy to the one or more tissue sites.

3. An apparatus, comprising:
an intravascularly-deliverable wireless stent electrode assembly comprising:
an expandable mechanical structure;
a plurality of at least partially overlapping induction coils attached to the expandable mechanical structure, and electrically insulated from the expandable mechanical structure, and from each other, the induction coils extending circumferentially along a longitudinal axis of the wireless stent electrode assembly and at least partially encircling the wireless stent electrode assembly, the induction coils configured to wirelessly receive magnetically-coupled energy;
one or more electrostimulation electrodes at least partially encircling the wireless stent electrode assembly, the one or more electrostimulation electrodes electrically connected to one or more of the plurality of induction coils, the one or more electrostimulation electrodes configured to deliver at least some of the received magnetically-coupled energy as an electrostimulation to one or more tissue sites;
wherein the plurality of induction coils are each deformable and each configured to open when the expandable mechanical structure is expanded;
wherein at least two of the plurality of induction coils are positioned at least partially orthogonally relative to each other; and
wherein each induction coil includes a laminar construction and is configured to be electrically insulated from one or more at least partially overlapping adjacent laminae, and electrically insulated from the expandable mechanical structure.

4. The apparatus of claim 3, including a control circuit within a lumen of the wireless stent electrode assembly.

5. The apparatus of claim 4, wherein the control circuit includes a rectifier circuit coupled to one or more of the induction coils, the rectifier circuit configured to rectify the magnetically-coupled energy received by the one or more of the induction coils.

6. The apparatus of claim 3, wherein at least three of the induction coils are positioned orthogonally relative to each other.

7. The apparatus of claim 3 wherein at least two of the induction coils are positioned radially relative the longitudinal axis of the stent.

8. An apparatus, comprising:
a plurality of intravascularly-deliverable stent electrode assemblies, each including an expandable mechanical structure and one or more electrostimulation electrodes;
a plurality of at least partially overlapping induction coils attached to at least one of the expandable mechanical structures, and electrically insulated from the expandable mechanical structure, and from each other, the one or more induction coils configured to receive magnetically-coupled energy;
wherein the one or more electrostimulation electrodes are configured to respectively deliver at least some of the received magnetically-coupled energy as an electrostimulation to one or more tissue sites;
wherein the one or more induction coils are deformable and configured to open when a corresponding expandable mechanical structure is expanded;
wherein the one or more induction coils are positioned orthogonally relatively to each other; and
wherein each induction coil includes a laminar construction and is configured to be electrically insulated from one or more at least partially overlapping adjacent laminae, and electrically insulated from the expandable mechanical structure.

9. The apparatus of claim 8, wherein at least one of the one or more electrostimulation electrodes comprises a first electrostimulation electrode configured to at least partially encircle a first expandable mechanical structure and wherein the electrostimulation is delivered between a first stent electrode assembly including the first electrode and a second stent electrode assembly including a second electrode.

10. The apparatus of claim 8, wherein at least one of the one or more electrostimulation electrodes extends from an end of at least one of the one or more induction coils.

11. The apparatus of claim 8, including a control circuit including an energy storage device, the energy storage device configured to store at least some of the magnetically-coupled energy received by at least one of the one or more induction coils, the energy storage device electrically connected to at least one of the one or more electrostimulation electrodes, and the energy storage device configured to supply the one or more electrostimulation electrodes with enough stored energy to deliver an electrostimulation to one or more tissue sites.

12. The apparatus of claim 8, wherein at least one of the one or more electrostimulation electrodes comprises a ring electrode that at least partially encircles a corresponding expandable mechanical structure.

13. The apparatus of claim 1, comprising a control circuit comprising an energy storage device electrically connected to the one or more induction coils, the energy storage device configured to store at least some of the magnetically-coupled energy, the control circuit configured to controllably adjust one or more electrostimulation parameters selected from a list including a pulse duration, a pulse timing, a pulse amplitude, or a pulse shape.

14. The apparatus of claim 1, wherein the elongate body is concentric with the expandable mechanical structure.

* * * * *

UNITED STATES PATENT AND TRADEMARK OFFICE
CERTIFICATE OF CORRECTION

PATENT NO. : 8,050,774 B2  
APPLICATION NO. : 11/316120  
DATED : November 1, 2011  
INVENTOR(S) : Graig L. Kveen et al.

Page 1 of 1

It is certified that error appears in the above-identified patent and that said Letters Patent is hereby corrected as shown below:

On the Title page, in field (75), in "Inventors", in column 1, line 1, delete "Crove," and insert -- Grove, --, therefor.

In column 18, line 43, in Claim 1, delete "long" and insert -- longitudinal --, therefor.

Signed and Sealed this  
Sixth Day of March, 2012

David J. Kappos  
*Director of the United States Patent and Trademark Office*